US008877960B2

(12) United States Patent
Nagamori et al.

(10) Patent No.: US 8,877,960 B2
(45) Date of Patent: Nov. 4, 2014

(54) FLUOROALKANESULFONIC ACID AMMONIUM SALTS AND METHOD FOR PRODUCING SAME

(75) Inventors: Masashi Nagamori, Fujimino (JP); Yuji Hagiwara, Kawagoe (JP); Takashi Masubuchi, Fujimino (JP); Satoru Narizuka, Saitama (JP)

(73) Assignee: Central Glass Company, Limited, Ube-shi (JP)

( * ) Notice: Subject to any disclaimer, the term of this patent is extended or adjusted under 35 U.S.C. 154(b) by 655 days.

(21) Appl. No.: 13/254,708

(22) PCT Filed: Mar. 12, 2010

(86) PCT No.: PCT/JP2010/054245
§ 371 (c)(1),
(2), (4) Date: Sep. 2, 2011

(87) PCT Pub. No.: WO2010/104177
PCT Pub. Date: Sep. 16, 2010

(65) Prior Publication Data
US 2011/0313190 A1  Dec. 22, 2011

(30) Foreign Application Priority Data

Mar. 12, 2009 (JP) ................................. 2009-058844
Mar. 11, 2010 (JP) ................................. 2010-054088

(51) Int. Cl.
*C07C 313/04* (2006.01)
*G03F 7/00* (2006.01)
*G03F 7/004* (2006.01)
*C07C 303/32* (2006.01)
*C07C 381/12* (2006.01)
*G03F 7/039* (2006.01)

(52) U.S. Cl.
CPC ........... *C07C 313/04* (2013.01); *C07C 2101/08* (2013.01); *G03F 7/0045* (2013.01); *G03F 7/0392* (2013.01); *C07C 2103/74* (2013.01); *C07C 2102/42* (2013.01); *C07C 2101/14* (2013.01); *C07C 303/32* (2013.01); *G03F 7/0046* (2013.01); *C07C 381/12* (2013.01)
USPC .......................................... 560/223; 560/129

(58) Field of Classification Search
CPC   C07C 303/32; C07C 313/04; C07C 2101/08; C07C 2103/74; C07C 2102/42; C07C 2101/14; C07C 381/12; G03F 7/0045; G03F 7/0392; G03F 7/0046

USPC .................................................. 560/129, 223
See application file for complete search history.

(56) References Cited

U.S. PATENT DOCUMENTS

| 6,749,987 | B2 | 6/2004 | Kodama et al. |
| 6,893,792 | B2 | 5/2005 | Miya et al. |
| 7,435,526 | B2 | 10/2008 | Kodama et al. |
| 7,511,169 | B2 | 3/2009 | Ohsawa et al. |
| 7,569,324 | B2 | 8/2009 | Kobayashi et al. |
| 7,776,512 | B2 | 8/2010 | Kodama et al. |
| 7,812,194 | B2 | 10/2010 | Kodama et al. |
| 2007/0298352 | A1 | 12/2007 | Kobayashi et al. |
| 2008/0124656 | A1 | 5/2008 | Kobayashi et al. |
| 2008/0182203 | A1 | 7/2008 | Yun et al. |
| 2008/0318160 | A1 | 12/2008 | Ohsawa et al. |
| 2010/0035185 | A1 | 2/2010 | Hagiwara et al. |
| 2010/0063232 | A1 | 3/2010 | Nagai et al. |
| 2010/0255419 | A1 | 10/2010 | Kodama et al. |
| 2013/0108962 | A1 | 5/2013 | Matsumura et al. |

FOREIGN PATENT DOCUMENTS

| JP | 2002-214774 A | 7/2002 |
| JP | 2004-4561 A | 1/2004 |
| JP | 2004-117959 A | 4/2004 |
| JP | 2007-145797 A | 6/2007 |
| JP | 2008-007409 A | 1/2008 |
| JP | 2008-7410 A | 1/2008 |
| JP | 2009-7327 A | 1/2009 |
| WO | WO 2008/029673 A1 | 3/2008 |
| WO | WO 2008/056795 A1 | 5/2008 |
| WO | WO 2008/099869 A1 | 8/2008 |
| WO | WO 2009/037980 A1 | 3/2009 |
| WO | WO 2009/037981 A1 | 3/2009 |

OTHER PUBLICATIONS

Corresponding International Search Report with English Translation dated May 11, 2010 (three (3) pages).
Form PCT/ISA/237 (four (4) pages, year 2010.
Korean-language Office Action dated Dec. 20, 2012 (Five (5) pages).
Japanese-language Office Action dated Feb. 13, 2014 (three (3) pages).

*Primary Examiner* — Yevegeny Valenrod
(74) *Attorney, Agent, or Firm* — Crowell & Moring LLP

(57) ABSTRACT

When sulfinating a carboxylic acid bromofluoroalkyl ester by using a sulfinating agent, an organic base is used, thereby obtaining a fluoroalkanesulfinic acid ammonium salt. This is oxidized to obtain a fluoroalkanesulfonic acid ammonium salt. This is used as the raw material and is converted to an onium salt or is converted to an onium salt by going through saponification and esterification, thereby obtaining a fluoroalkanesulfonic acid onium salt. This fluoroalkanesulfonic acid onium salt is useful as a photoacid generator used for chemically amplified resist materials, etc.

10 Claims, No Drawings

FLUOROALKANESULFONIC ACID AMMONIUM SALTS AND METHOD FOR PRODUCING SAME

TECHNICAL FIELD

The present invention relates to fluorine-containing sulfonic acid salts and their production method, which are useful as an intermediate for producing a photoacid generator, which is useful as a chemically amplified resist material suitable for a micro-processing technology, particularly photolithography, in the production steps of semiconductor devices and the like. Furthermore, the present invention relates to a method for producing fluorine-containing sulfonic acid onium salts, which behave as a photoacid generator.

BACKGROUND OF THE INVENTION

In recent years, the trend toward micro-scale pattern rule has been increasing rapidly with the trend toward large-scale integration and high-speed of LSI. The trend toward a shorter wavelength of the exposure light source lies behind it. For example, it has become possible to mass-produce DRAM (dynamic random-access memory) of 64M-bits (processing dimension is 0.25 μm or less) by the wavelength shortening from mercury lamp i-line (365 nm) to KrF excimer laser (248 nm). Furthermore, in order to realize the production of DRAM's having integration degrees of 1 G or greater, a lithography using ArF excimer laser (193 nm) is used.

As a resist suitable for such exposure wavelength, "chemically amplified resist material" attracts much attention. This contains a radiosensitive acid generator (hereinafter referred to as "photoacid generator"), which generates an acid by radiation irradiation (hereinafter, referred to as "exposure"), and is a pattern-forming material that forms a pattern by making a difference in solubility between the exposed portion and the unexposed portion through a reaction using the acid generated by the exposure as a catalyst.

Various studies have also been conducted with respect to a photoacid generator used for such chemically amplified resist material. In case that a photoacid generator that generates an alkane or arenesulfonic acid, as used for chemically amplified resist materials, for which a conventional KrF excimer laser light is used as the light source, is used as a component of the above ArF chemically amplified resist materials, it is known that acid strength for severing an acid-labile group of the resin is not sufficient, resulting in no possibility of resolution at all, or it is known to be not suitable for the device production due to low sensitivity.

Therefore, as a photoacid generator of ArF chemically amplified resist materials, one that generates a perfluoroalkanesulfonic acid, which is high in acid strength, is generally used. Perfluorooctanesulfonic acid, or its derivatives are, however, known as PFOS by its initials, and stability (undegradability) and hydrophobicity resulting from C—F bond, and ecological concentration and accumulation resulting from oleophilicity have become problems. Furthermore, a perfluoroalkanesulfonic acid having a carbon number of 5 or greater or its derivatives also pose the above problems.

To deal with problems related to such PFOS, there is conducted by each place the development of a partially fluorine-substituted alkanesulfonic acid having a lowered fluorine substitution rate. For example, there have been the developments of alkoxycarbonylfluoromethanesulfonic acid onium salts as acid generators, such as triphenylsulfonium methoxycarbonyldifluoromethanesulfonato (Patent Publication 1), (4-methylphenyl)diphenylsulfonyl t-butoxycarbonyldifluoromethane sulfonato (Patent Publication 2), or triphenylsulfonium (adamantan-1-ylmethyl)oxycarbonyldifluoromethanesulfonato (Patent Publication 3).

On the other hand, there has been the development of triphenylsulfonium 1,1,3,3,3-pentafluoro-2-benzoyloxypropane-1-sulfonato or the like, which is one type of alkylcarbonyloxyalkane sulfonic acid onium salts, of which ester bond is opposite to that of the above-mentioned alkoxycarbonyldifluoromethanesulfonic acid onium salts (Patent Publication 4).

The present applicant has found a 2-alkylcarbonyloxy-1,1-difluoroethanesulfonic acid onium salt, in which the number of fluorines is less by three than that of the acid generator of Patent Publication 4, which is considered to be less in adverse effects on the environment, and has obtained findings that this substance functions as an acid generator having a strong acidity by the minimum number of fluorine atoms, is superior in terms of compatibility with solvent and resin, and is useful as an acid generator for resists (Patent Publication 5).

Furthermore, the present applicants have found a polymerizable tetrafluoroalkanesulfonic acid onium salt, which is a similar alkylcarbonyloxyalkanesulfonic acid onium salt, but the number of fluorines is less by one than that of the acid generator of Patent Publication 4, which is considered to be less in adverse effects on the environment (Patent Publication 6).

Here, as a method for synthesizing the polymerizable tetrafluoroalkanesulfonic acid onium salt of Patent Publication 6, there is disclosed a reaction pathway shown in the following reaction formula [1].

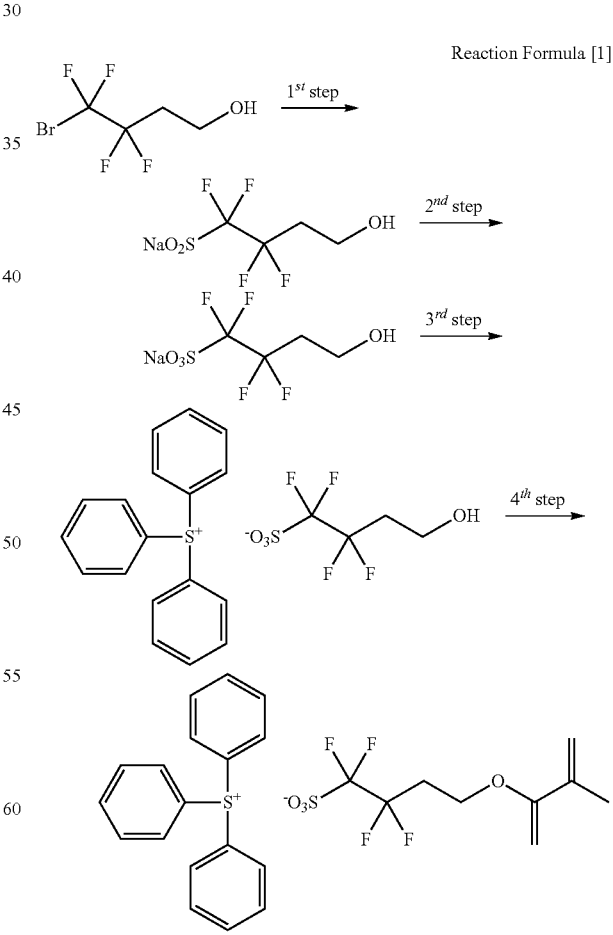

Reaction Formula [1]

That is, it is a pathway equipped with a first step of obtaining a sulfinic acid metal salt by sulfinating 4-bromo-3,3,4,4-tetrafluorobutan-1-ol using a sulfinating agent, a second step of obtaining a sulfonic acid metal salt by oxidizing the obtained sulfinic acid metal salt using an oxidizing agent, a third step of obtaining a sulfonic acid onium salt by furthermore reacting the obtained sulfonic acid metal salt with a monovalent onium salt, and a fourth step of obtaining the target polymerizable sulfonic acid onium salt by reacting the obtained sulfonic acid onium salt with an alkylacrylic halide or alkylacrylic anhydride.

Furthermore, a similar tetrafluoroalkanesulfonic acid onium salt is disclosed in another publication, too (Patent Publication 7). In the publication, there is disclosed a synthesis method by using 1,4-dibromo-1,1,2,2-tetrafluorobutane as the starting material, and converting it into an aliphatic or aromatic carboxylic acid 4-bromo-3,3,4,4-tetrafluorobutyl ester by a selective substitution reaction using a carboxylate such as sodium carboxylate or ammonium carboxylate, and thereafter similar to Patent Publication 6 reacting the ester with a sulfine oxidizer such as sodium dithionite, in the presence of a base such as sodium hydrogencarbonate, in water, acetonitrile or a mixture thereof as a solvent to produce 4-acyloxy-1,1,2,2-tetrafluorobutanesulfinic acid salt, and then conducting an oxidization by a usual method by an oxidizer such as hydrogen peroxide solution in water as solvent in the presence of sodium tungstate.

PRIOR ART PUBLICATIONS

Patent Publications

Patent Publication 1: Japanese Patent Application Publication No. 2004-117959
Patent Publication 2: Japanese Patent Application Publication No. 2002-214774
Patent Publication 3: Japanese Patent Application Publication No. 2004-4561
Patent Publication 4: Japanese Patent Application Publication No. 2007-145797
Patent Publication 5: Japanese Patent Application Publication No. 2009-7327
Patent Publication 6: International Patent Application Publication 2008/056795 Pamphlet
Patent Publication 7: Japanese Patent Application Publication No. 2008-7410

SUMMARY OF THE INVENTION

In the method of the above reaction formula [1] described in Patent Publication 6, for producing a fluoroalkanesulfonic acid onium salt, of which number of fluorines is two or greater, the obtained target products are low in purity (80% and 78%) not only in the sulfinating step of the first step but also in the oxidizing step of the second step. Furthermore, the yields are respectively computed at 77% and 88% from the weights of the obtained target products without considering purity. If purity is considered, they are respectively 62% and 69%, which are not necessarily high. Furthermore, most of the impurities are sodium salts, of which residence in the photoacid generator of the final product is inappropriate.

As a main cause of generating such problem, it is possible to point out that the sulfinic acid metal salt and the sulfonic acid metal salt as the target products are easily soluble in water and scarcely soluble in organic solvents. In the case of Patent Publication 6, acetonitrile is used as an extracting solvent in the sulfinating step of the first step. This is because it is difficult to sufficiently dissolve or extract the target sulfinic acid metal salt by other non-water-soluble organic solvents. As is generally known, acetonitrile has a high power to dissolve organic matters, but is water-soluble. Therefore, recovery of the extract is not so high, and water contamination becomes a lot. As a result, it lowers yield of the target product, and causes contamination by water-soluble inorganic impurities. Furthermore, in the oxidation step of the second step, water is used as the reaction solvent, and the water is distilled off. In this case, of the impurities generated, non-volatile substances become particularly problematic, and it is not possible to remove the metal salt such as sodium salt.

In the method of Patent Publication 7 too, a similar problem exists since yield is not necessarily high.

Thus, some obstacles exist in the production of fluoroalkanesulfonic acid onium salts. Therefore, there was a demand for establishing an industrial production method capable of easily producing a fluoroalkanesulfonic acid onium salt skeleton with a low cost.

As mentioned above, it is a task of the present invention to provide a method for easily producing fluoroalkanesulfonic acid salts, which are useful as a photoacid generator used for chemically-amplified resist materials, etc., with a low cost.

The present inventors repeated an eager study to solve the task. As a result, the inventors have found novel compounds useful for producing the above-mentioned fluoroalkanesulfonic acid onium salts. Then, we have found novel reaction routes that go through these novel compounds and are considerably advantageous in a large-scale synthesis as compared with conventional methods.

The invention of the present application contains [Mode 1] to [Mode 4] as shown in the following.

[Mode 1]

Firstly, we conducted a study on the method for synthesizing a fluoroalkanesulfinic acid ammonium salt, which becomes a raw material compound common to the entirety of the invention of the present application.

Hitherto, to obtain a terminal difluoroalkylsulfinic acid salt by sulfinating a terminal bromodifluoroalkyl group, there has been taken in general a method of using sodium dithionite as a sulfinating agent in a mixed solvent of a polar solvent, such as N,N-dimethylformamide (DMF), acetonitrile or methanol, and water. In this case, the sulfinated body is obtained as a sulfinic acid sodium salt (e.g., Journal of Fluorine Chemistry, Vol. 67, page 233 to page 234, 1994).

In the case of a carboxylic acid bromofluoroalkyl ester too that is a raw material compound used in the invention of the present application and is represented by the following general formula [1],

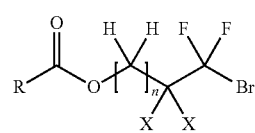

[1]

(In the general formula [1], R represents a $C_{1-10}$ straight-chain or branched alkyl group, a $C_{3-20}$ alicyclic organic group, an organic group formed of a $C_{3-20}$ alicyclic organic group and a straight-chain alkylene group, a $C_{3-30}$ monocyclic or polycyclic lactone, or $C_{6-20}$ aryl group. (Herein, hydrogen atoms on the alkyl group, the alicyclic organic group, the organic group formed of the alicyclic organic group and the straight-chain alkylene group, the monocyclic or polycyclic lactone, and the aryl group may partially or completely be replaced with fluorine, hydroxyl group, hydroxycarbonyl group, or a $C_{1-6}$ straight-chain, branched or cyclic alkoxy group. Furthermore, two hydrogen atoms on the same carbon forming the alkyl group, the alicyclic organic group or the organic group formed of the alicyclic organic group and the straight-chain alkylene group may be replaced with one oxygen atom to become a keto group. However, one having a nonconjugated unsaturated moiety (a double bond or triple bond) in the structure is excluded as R. Each X independently represents a group selected from the group consisting of hydrogen atom, fluorine atom, a $C_{1-6}$ alkyl group, and a $C_{1-6}$ fluorine-containing alkyl group. n represents an integer of 1-8.)

it is possible to obtain the corresponding sulfinic acid sodium salt represented by the following general formula [13]

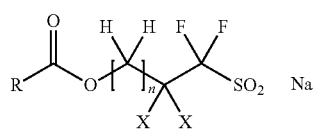

[13]

(In the general formula [13], R and X have the same meanings as those of R and X in the general formula [1]) by using sodium dithionite in a mixed solvent of a polar solvent, such as DMF, acetonitrile or methanol, and water.

In this reaction, however, similar to the results mentioned in Journal of Fluorine Chemistry, Vol. 67, page 233 to page 234, 1994, depending on the combination of solvents, the reaction does not proceed at all, or it is extremely difficult to complete the reaction. Like a combination of ethanol and water, particularly in case that the reaction liquid becomes homogeneous, it is difficult to complete the reaction. Like a combination of acetonitrile and water, in case that the reaction liquid can be separated into two layers (organic layer and aqueous layer) by appropriately adjusting the condition, it becomes possible to finally complete the reaction by separating the aqueous layer from the reaction liquid in the middle of the reaction and adding again water and sodium dithionite (see Comparative Example 1-1 and Comparative 1-2).

Furthermore, in order to take out the target sulfinic acid sodium salt after the reaction, it is necessary to distill out the solvent containing water by a large amount, thereby causing a large burden. Furthermore, a side reaction produces a trace amount of fluoride ions. As the reaction liquid is concentrated without removing this fluoride ion, the remaining fluoride ion concentration increases gradually. Therefore, when a glass apparatus is used, this is corroded (see Comparative Example 1-1).

Furthermore, in the present reaction, bromine released from the raw material carboxylic acid bromofluoroalkyl ester is converted to sodium bromide by probably sodium of sodium dithionite to exist in the system. If concentration is conducted without removing this and if it is subjected to the oxidation step of the next step without separation from the target sulfinic acid sodium salt, there were many problems such as the formation of by-products (see Comparative Example 2-1 and Comparative Example 2-2).

Thus, as a result of an eager study, the present inventors have found that almost only an ammonium salt, not sodium salt, is obtained by adding at the time of the sulfinating reaction an amine that is at least an equivalent of the carboxylic acid bromofluoroalkyl ester, together with the sulfinating agent. The ammonium salt is a novel compound represented by the following general formula [2]

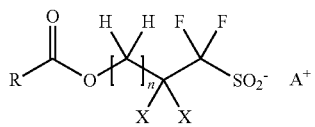

[2]

(In the general formula [2], R and X have the same meanings as those of R and X in the general formula [1]. $A^+$ represents an ammonium ion derived from the amine.). Since this sulfinic acid ammonium salt is high in lipophilicity and low in hydrophilicity, it is possible to easily conduct extraction with an organic solvent. Therefore, we also have found that inorganic salts, such as fluoride ion and sodium bromide, that were problematic can be removed by washing with water. We have obtained findings that doing so results in no limitation on the reactor and that side reactions in the oxidation step of the next step can be suppressed.

Surprisingly, we also have found a fact that the sulfinating reaction is greatly accelerated and completed in a short time by making the amine coexistent.

Furthermore, the present inventors have obtained findings that, after the above-mentioned extraction with an organic solvent, if the organic layer is washed with a thiosulfuric acid metal salt aqueous solution or sulfurous acid metal salt aqueous solution, not only an efficient purification of the fluoroalkanesulfinic acid salt can be made, but also the formation of by-products (the carboxylic acid bromofluoroalkyl ester represented by the general formula [1], which is the substrate of the sulfinating reaction: it disappears by the sulfinating step, but is formed again by the oxidation step) in the subsequent oxidation step can remarkably be suppressed.

Thus, the present inventors have found fluoroalkanesulfinic acid salts, which are useful as an intermediate for producing photoacid generators for resist or as an intermediate for producing solid polymer electrolytes for fuel cell, and their novel production method and purification method, which are suitable for a large-scale production.

[Mode 2]

We have found that a fluoroalkanesulfonic acid ammonium salt represented by general formula [3]

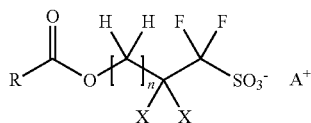

[3]

(In the general formula [3], R, X and $A^+$ have the same meanings as R, X and $A^+$ in general formula [2].)

can be obtained by firstly subjecting a fluoroalkanesulfinic acid ammonium salt represented by general formula [2] and obtained by the method (this is also referred to as the first step) of the above Mode 1 to an oxidation step that is the second step.

Since this sulfonic acid ammonium salt is high in lipophilicity and low in hydrophilicity, similar to the sulfinic acid ammonium salt, it is possible to easily conduct extraction with an organic solvent. Therefore, we have found findings that a high-purity sulfonic acid ammonium salt can be obtained by removing water-soluble impurities containing inorganic salts by washing with water.

Thus, the present inventors have found novel production method and purification method, which are suitable for a large-scale production, of fluoroalkanesulfonic acid ammonium salts, which are useful as an intermediate for producing photoacid generators for resist or as an intermediate for producing solid polymer electrolytes for fuel cell.

[Mode 3]

We have found that a fluoroalkanesulfonic acid onium salt represented by general formula [5] can be obtained by subsequently subjecting a fluoroalkanesulfonic acid ammonium salt represented by general formula [3] and synthesized by the method of the above [Mode 2] to an onium salt exchange step 1 (the third step) (see the following reaction formula [3]).

Reaction formula [3]

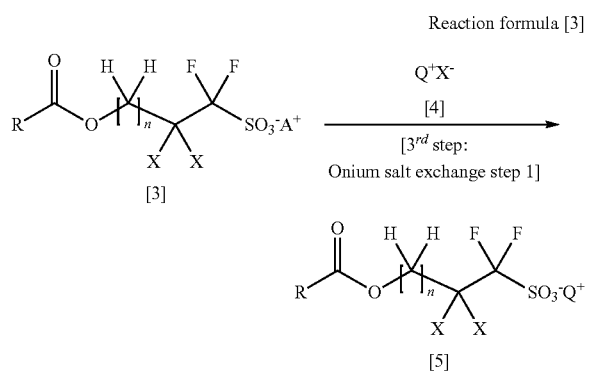

(In the above reaction formula [3], R, X and $A^+$ have the same meanings as R, X and $A^+$ in general formula [2]. $X^-$ represents a monovalent anion. $Q^+$ represents a sulfonium cation represented by the following general formula (a) or the following general formula (b), or an iodonium cation represented by the following general formula (c).

(a)

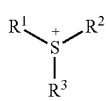

In the above general formula (a), $R^1$, $R^2$ and $R^3$ mutually independently represent substituted or unsubstituted $C_{1-10}$ straight-chain or branched alkyl groups, alkenyl groups or oxoalkyl groups; or substituted or unsubstituted $C_{6-18}$ aryl groups, aralkyl groups or aryloxoalkyl groups; or any two or more of $R^1$, $R^2$ and $R^3$ may be connected with each other to form a ring together with the sulfur atom in the formula.

(b)

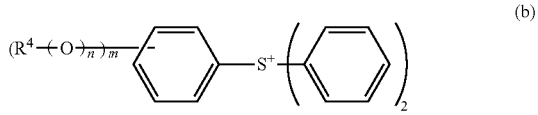

In the above general formula (b), $R^4$ represents a substituted or unsubstituted $C_{1-20}$ straight-chain, branched or cyclic alkyl group or alkenyl group; or substituted or unsubstituted $C_{6-14}$ aryl group. m represents an integer of 1-5, and n represents 0 (zero) or 1.

(c)

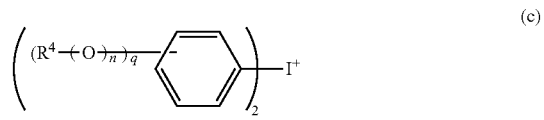

In the above general formula (c), $R^4$ represents a substituted or unsubstituted $C_{1-20}$ straight-chain, branched or cyclic alkyl group or alkenyl group; or substituted or unsubstituted $C_{6-14}$ aryl group. q represents an integer of 0 (zero) to 5, and n represents 0 (zero) or 1.)

That is, it became possible to synthesize a fluoroalkanesulfonic acid onium salt, which is useful as a photoacid generator used for chemically-amplified resist materials, by the method of this [Mode 3].

[Mode 4]

As mentioned above, there is a limitation in the type of the functional group R of the compound that can be synthesized by [Mode 3]. That is, the functional group R of the compound that can be synthesized by [Mode 3] represents a $C_{1-10}$ straight-chain or branched alkyl group, a $C_{3-20}$ alicyclic organic group, an organic group formed of a $C_{3-20}$ alicyclic organic group and a straight-chain alkylene group, a $C_{3-30}$ monocyclic or polycyclic lactone, or $C_{6-20}$ aryl group. (Herein, hydrogen atoms on the alkyl group, the alicyclic organic group, the organic group formed of the alicyclic organic group and the straight-chain alkylene group, the monocyclic or polycyclic lactone, and the aryl group may partially or completely be replaced with fluorine, hydroxyl group, hydroxycarbonyl group, or a $C_{1-6}$ straight-chain, branched or cyclic alkoxy group. Furthermore, two hydrogen atoms on the same carbon forming the alkyl group, the alicyclic organic group or the organic group formed of the alicyclic organic group and the straight-chain alkylene group may be replaced with one oxygen atom to become a keto group. However, one having a nonconjugated unsaturated moiety (a double bond or triple bond) in the structure is excluded as R.). As R, one having in its structure a nonconjugated unsaturated moiety (a double bond or triple bond) other than an aromatic ring having a conjugated unsaturated moiety, such as aryl group or heteroaryl group, is excluded. This is caused by the first step (sulfinating step). That is, the inventors have found that, if one having in its structure as R a nonconjugated unsaturated moiety (a double bond or triple bond) is used as a raw material of the first step (sulfinating step), the nonconjugated unsaturated moiety generates a side reaction, and therefore it is difficult to obtain the target sulfinated product.

R having a nonconjugated unsaturated moiety (a double bond or triple bond) can be exemplified by straight-chain, branched or cyclic alkenyl groups. As such alkenyl groups, specifically, it is possible to cite vinyl group, allyl group, 1-methylethenyl group, 1-methylallyl group, 2-methylallyl group, 1-propenyl group, isopropenyl group, 2-butenyl group, 3-butenyl group, 1,3-butadienyl group, 2-pentenyl group, 4-pentenyl group, 2-hexenyl group, 5-hexenyl group, cyclopropenyl group, cyclopentenyl group, cyclohexenyl group, 5-norbornen-1-yl group, etc. (the following reaction formula [4]; Comparative Example [3]).

Reaction formula [4]

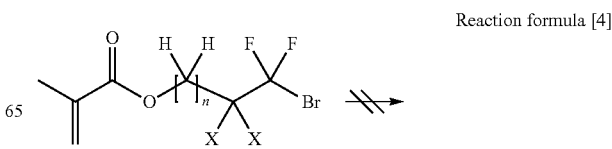

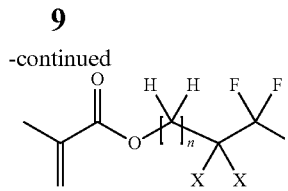

In view of such condition, the present inventors have found a novel synthesis route in which a fluoroalkanesulfonic acid ammonium salt represented by general formula [3] obtained by the above [Mode 2] is used as a starting material, and have reached findings that the above problem can be solved by taking the route.

That is, we have found that it is possible to obtain a fluoroalkanesulfonic acid onium salt represented by general formula [10]

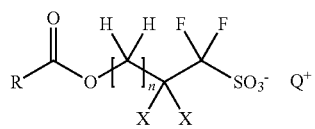

[10]

(see the following reaction formula [6]), which is characterized by that firstly a fluoroalkanesulfonic acid ammonium salt represented by general formula [3] and obtained by the above [Mode 2] is subjected to a saponification reaction (a hydrolysis reaction in the presence of a basic substance) (the 3' step: saponification step) to obtain a hydroxyfluoroalkanesulfonic acid salt represented by general formula [6]

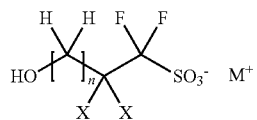

[6]

(In the above general formula [6], $M^+$ represents a counter cation. Each X independently represents a group selected from the group consisting of hydrogen atom, fluorine atom, a $C_{1-6}$ alkyl group, and $C_{1-6}$ fluorine-containing alkyl group. n represents an integer of 1-8.)

then an onium salt exchange (the fourth step: an onium salt exchange step 2) is conducted by using a monovalent onium salt represented by general formula [4]

$$Q^+X^-$$ [4]

to obtain a hydroxyfluoroalkanesulfonic acid onium salt represented by general formula [9]

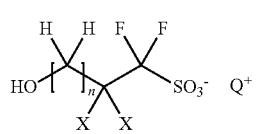

[9]

and furthermore there is conducted a reaction (the fifth step: esterification step 2) with a carboxylic acid derivative represented by general formula [7]

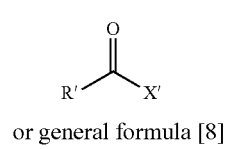

[7]

or general formula [8]

[8]

(In the above general formulas [7] and [8], X' represents a hydroxyl group or halogen. In the above general formulas [7] and [8], R' represents a $C_{1-10}$ straight-chain or branched alkyl group, a $C_{1-10}$ straight-chain or branched alkenyl group having a polymerizable double bond at an end portion at least, a $C_{3-20}$ alicyclic organic group, an organic group formed of a $C_{3-20}$ alicyclic organic group and a straight-chain alkylene group, a $C_{3-30}$ monocyclic or polycyclic lactone, or a $C_{6-20}$ aryl group (Herein, hydrogen atoms on the alkyl group, the alkenyl group, the alicyclic organic group, the organic group formed of the alicyclic organic group and the straight-chain alkylene group, the monocyclic or polycyclic lactone, and the aryl group may partially or entirely be replaced with fluorine, hydroxyl group, hydroxycarbonyl group, or $C_{1-6}$ straight-chain, branched or cyclic alkoxy group. Furthermore, two hydrogen atoms on the same carbon constituting the alkyl group, the alkenyl group, the alicyclic organic group, or the organic group formed of the alicyclic organic group and the straight-chain alkylene group may be replaced with a single oxygen atom to make a keto group. Furthermore, one of the hydrogen atoms on the alkyl group may be replaced with 2-acryloyloxy group or 2-methacryloyloxy group.).

Reaction formula [6]

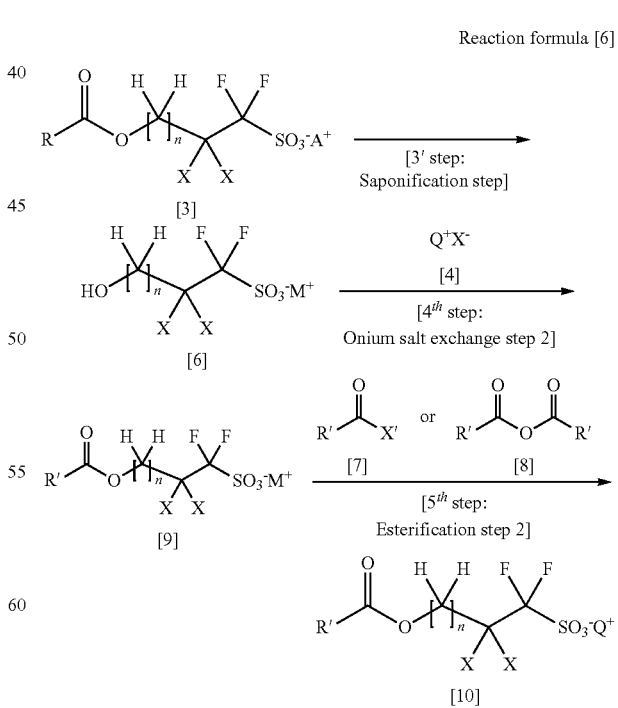

Herein, as the substituent R' of the fluoroalkanesulfonic acid onium salt represented by formula [10], a point that one having a nonconjugated unsaturated moiety (a double bond or triple bond) in the structure is also contained is important. That is, this [Mode 4] is particularly useful for one having a nonconjugated unsaturated moiety in the structure as the substituent R', of fluoroalkanesulfonic acid onium salts useful as photoacid generators used for chemically-amplified resist materials.

In particular, one having a nonconjugated unsaturated moiety at an end of the substituent, that is, a (ω-alkenylcarbonyloxy)fluoroalkanesulfonic acid onium salt, for example, as disclosed in International Patent Publication 2006/121096, can be fixed in a resist resin by conducting a copolymerization with another monomer. With this, it can be used as a resist resin supported type photoacid generator. Such a resist resin supported type photoacid generator is a new type of photoacid generator, which attracts attention in recent years, due to high performances such as high resolution. In that sense too, a (ω-alkenylcarbonyloxy)fluoroalkanesulfonic acid onium salt having a nonconjugated unsaturated moiety at an end of the substituent is extremely useful.

As mentioned above, it is possible to produce fluoroalkanesulfonic acid salts, which are useful as an intermediate of acid generators used for resist materials or useful as an electrolyte intermediate for fuel cells, and fluoroalkanesulfonic acid onium salts, which are useful as photoacid generators, with respect to compounds of wide substituents, thereby reaching the completion of the present invention.

In the reactions of the present invention, each of necessary raw materials has a low price, the operation at each step is simple, and implementation is possible with a low burden in operation. Therefore, it is far advantageous in terms of producing the target fluoroalkanesulfonic acid salts in an industrial scale, than conventional means That is, the present invention contains [Invention 1] to [Invention 10].

[Invention 1]

A fluoroalkanesulfinic acid ammonium salt characterized by being represented by the following general formula [2].

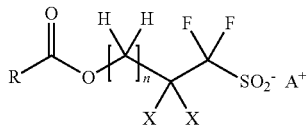

[2]

(In the above general formula [2], $A^+$ represents an ammonium ion, and R represents a $C_{1-10}$ straight-chain or branched alkyl group, a $C_{3-20}$ alicyclic organic group, an organic group formed of a $C_{3-20}$ alicyclic organic group and a straight-chain alkylene group, a $C_{3-30}$ monocyclic or polycyclic lactone, or $C_{6-20}$ aryl group. (Herein, hydrogen atoms on the alkyl group, the alicyclic organic group, the organic group formed of the alicyclic organic group and the straight-chain alkylene group, the monocyclic or polycyclic lactone, and the aryl group may partially or completely be replaced with fluorine, hydroxyl group, hydroxycarbonyl group, or a $C_{1-5}$ straight-chain, branched or cyclic alkoxy group. Furthermore, two hydrogen atoms on the same carbon forming the alkyl group, the alicyclic organic group or the organic group formed of the alicyclic organic group and the straight-chain alkylene group may be replaced with one oxygen atom to become a keto group. However, one having a nonconjugated unsaturated moiety (a double bond or triple bond) in the structure is excluded as R.) Each X independently represents a group selected from the group consisting of hydrogen atom, fluorine atom, a $C_{1-6}$ alkyl group, and a $C_{1-6}$ fluorine-containing alkyl group. n represents an integer of 1-8.)

[Invention 2]

A salt according to Invention 1, wherein $A^+$ is an ammonium ion represented by general formula [I].

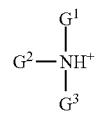

[I]

(In the above general formula [I], $G^1$, $G^2$ and $G^3$ mutually independently represent hydrogen atoms, $C_{1-6}$ alkyl groups, $C_{1-6}$ alkoxyalkyl groups, $C_{3-12}$ cycloalkyl groups, optionally substituted phenyl groups, optionally substituted $C_{7-12}$ aralkyl groups, optionally substituted naphthyl groups, optionally substituted $C_{5-10}$ hetero aromatic groups, or a ring optionally containing a hetero atom by at least two of $G^1$, $G^2$ and $G^3$.)

[Invention 3]

A method for producing a fluoroalkanesulfinic acid ammonium salt represented by general formula [2]

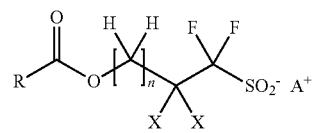

[2]

by reacting a carboxylic acid bromofluoroalkyl ester represented by the following general formula [1]

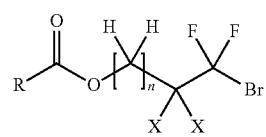

[1]

with a sulfinating agent in the presence of an amine.

(In the above general formula [1] and general formula [2], R represents a $C_{1-10}$ straight-chain or branched alkyl group, a $C_{3-20}$ alicyclic organic group, an organic group formed of a $C_{3-20}$ alicyclic organic group and a straight-chain alkylene group, a $C_{3-30}$ monocyclic or polycyclic lactone, or $C_{6-20}$ aryl group. (Herein, hydrogen atoms on the alkyl group, the alicyclic organic group, the organic group formed of the alicyclic organic group and the straight-chain alkylene group, the monocyclic or polycyclic lactone, and the aryl group may partially or completely be replaced with fluorine, hydroxyl group, hydroxycarbonyl group, or a $C_{1-6}$ straight-chain, branched or cyclic alkoxy group. Furthermore, two hydrogen atoms on the same carbon forming the alkyl group, the alicyclic organic group or the organic group formed of the alicyclic organic group and the straight-chain alkylene group may be replaced with one oxygen atom to become a keto group. However, one having a nonconjugated unsaturated moiety (a double bond or triple bond) in the structure is excluded as R.) $A^+$ represents an ammonium ion. Each X independently represents a group selected from the group consisting of hydrogen atom, fluorine atom, a $C_{1-6}$ alkyl group, and a $C_{1-6}$ fluorine-containing alkyl group. n represents an integer of 1-8.)

[Invention 4]

A method for producing a fluoroalkanesulfonic acid ammonium salt represented by general formula [3]

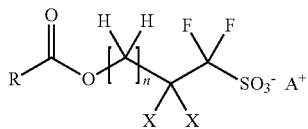
[3]

by comprising the following two steps.

The first step (sulfinating step): a step of obtaining a fluoroalkanesulfinic acid ammonium salt represented by general formula [2]

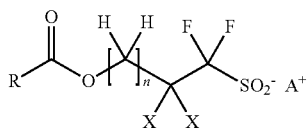
[2]

by reacting a carboxylic acid bromofluoroalkyl ester represented by the following general formula [1]

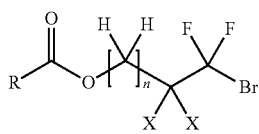
[1]

with a sulfinating agent in the presence of an amine.

The second step (oxidation step): a step of obtaining a fluoroalkanesulfonic acid ammonium salt represented by general formula [3] by reacting the fluoroalkanesulfinic acid ammonium salt represented by general formula [2] and obtained by the first step (sulfinating step), with an oxidizing agent.

(In the above general formula [1] to general formula [3], R represents a $C_{1-10}$ straight-chain or branched alkyl group, a $C_{3-20}$ alicyclic organic group, an organic group formed of a $C_{3-20}$ alicyclic organic group and a straight-chain alkylene group, a $C_{3-30}$ monocyclic or polycyclic lactone, or $C_{6-20}$ aryl group. (Herein, hydrogen atoms on the alkyl group, the alicyclic organic group, the organic group formed of the alicyclic organic group and the straight-chain alkylene group, the monocyclic or polycyclic lactone, and the aryl group may partially or completely be replaced with fluorine, hydroxyl group, hydroxycarbonyl group, or a $C_{1-6}$ straight-chain, branched or cyclic alkoxy group. Furthermore, two hydrogen atoms on the same carbon forming the alkyl group, the alicyclic organic group or the organic group formed of the alicyclic organic group and the straight-chain alkylene group may be replaced with one oxygen atom to become a keto group. However, one having a nonconjugated unsaturated moiety (a double bond or triple bond) in the structure is excluded as R.) $A^+$ represents an ammonium ion. Each X independently represents a group selected from the group consisting of hydrogen atom, fluorine atom, a $C_{1-6}$ alkyl group, and a $C_{1-6}$ fluorine-containing alkyl group. n represents an integer of 1-8.)

[Invention 5]

A method for producing a fluoroalkanesulfonic acid onium salt represented by general formula [5]

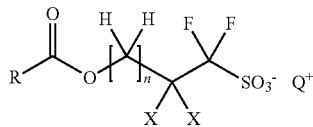
[5]

characterized by that the fluoroalkanesulfonic acid ammonium salt represented by general formula [3] and obtained by the method of Invention 4 is subjected to an onium salt exchange (the third step: onium salt exchange step 1) by using a monovalent onium salt represented by general formula [4].

$$Q^+X^-$$ [4]

(In the above general formula [4], $X^-$ represents a monovalent anion. In the above general formula [5], R has the same meaning as that of R in general formula [1] to general formula [3]. In the above general formula [4] and general formula [5], $Q^+$ represents a sulfonium cation represented by the following general formula (a) or the following general formula (b), or an iodonium cation represented by the following general formula (c).

(a)

In the above general formula (a), $R^1$, $R^2$ and $R^3$ mutually independently represent substituted or unsubstituted $C_{1-10}$ straight-chain or branched alkyl groups, alkenyl groups or oxoalkyl groups; or substituted or unsubstituted $C_{6-18}$ aryl groups, aralkyl groups or aryloxoalkyl groups; or any two or more of $R^1$, $R^2$ and $R^3$ may be connected with each other to form a ring together with the sulfur atom in the formula.

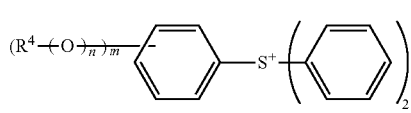
(b)

In the above general formula (b), $R^4$ represents a substituted or unsubstituted $C_{1-20}$ straight-chain, branched or cyclic alkyl group or alkenyl group; or substituted or unsubstituted $C_{6-14}$ aryl group. m represents an integer of 1-5, and n represents 0 (zero) or 1.

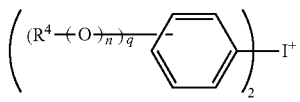
(c)

In the above general formula (c), $R^4$ represents a substituted or unsubstituted $C_{1-20}$ straight-chain, branched or cyclic alkyl group or alkenyl group; or substituted or unsubstituted $C_{6-14}$ aryl group. q represents an integer of 0 (zero) to 5, and n represents 0 (zero) or 1.

[Invention 6]

A method for producing a fluoroalkanesulfonic acid onium salt represented by general formula [10]

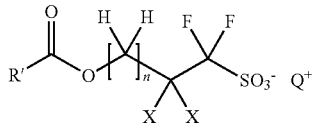
[10]

which is characterized by that a fluoroalkanesulfonic acid ammonium presented by general formula [3] and obtained by the method of Invention 4 is subjected to a saponification (the 3' step: saponification step) to obtain a hydroxyfluoroalkanesulfonic acid salt represented by general formula [6]

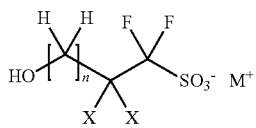
[6]

then an onium salt exchange (the fourth step: an onium salt exchange step 2) is conducted by using a monovalent onium salt represented by general formula [4]

$$Q^+X^-  \quad [4]$$

to obtain a hydroxyfluoroalkanesulfonic acid onium salt represented by general formula [9]

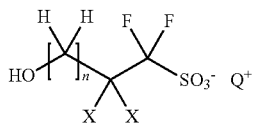
[9]

and furthermore there is conducted a reaction (the fifth step: esterification step 2) with a carboxylic acid derivative represented by general formula [7]

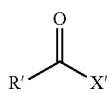
[7]

or general formula [8].

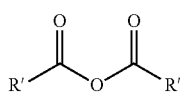
[8]

(In the above general formula [6] and general formula [9], $M^+$ represents a counter cation. In the above general formula [7], X' represents a hydroxyl group or halogen. In the above general formulas [7] to general formula [10], R' represents a $C_{1-10}$ straight-chain or branched alkyl group, a $C_{1-10}$ straight-chain or branched alkenyl group having a polymerizable double bond at an end portion at least, a $C_{3-20}$ alicyclic organic group, an organic group formed of a $C_{3-20}$ alicyclic organic group and a straight-chain alkylene group, a $C_{3-30}$ monocyclic or polycyclic lactone, or a $C_{6-20}$ aryl group (Herein, hydrogen atoms on the alkyl group, the alkenyl group, the alicyclic organic group, the organic group formed of the alicyclic organic group and the straight-chain alkylene group, the monocyclic or polycyclic lactone, and the aryl group may partially or entirely be replaced with fluorine, hydroxyl group, hydroxycarbonyl group, or $C_{1-6}$ straight-chain, branched or cyclic alkoxy group. Furthermore, two hydrogen atoms on the same carbon constituting the alkyl group, the alkenyl group, the alicyclic organic group, or the organic group formed of the alicyclic organic group and the straight-chain alkylene group may be replaced with a single oxygen atom to make a keto group. Furthermore, one of the hydrogen atoms on the alkyl group may be replaced with 2-acryloyloxy group or 2-methacryloyloxy group.). In the above general formula [10], $Q^+$ has the same meaning as that of $Q^+$ in general formula [4] and general formula [5]. Each X independently represents a group selected from the group consisting of hydrogen atom, fluorine atom, a $C_{1-6}$ alkyl group, and $C_{1-6}$ fluorine-containing alkyl group. n represents an integer of 1-8.)

[Invention 7]

A method according to any one of Invention 3 to Invention 6, which is characterized by that, in any one of Invention 3 to Invention 6, the carboxylic acid bromofluoroalkyl ester is one obtained by an esterification of a bromofluoro alcohol represented by the following general formula [A]

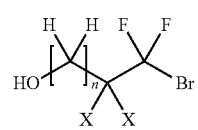
[A]

(In the above general formula [A], each X independently represents a group selected from the group consisting of hydrogen atom, fluorine atom, a $C_{1-6}$ alkyl group, and $C_{1-6}$ fluorine-containing alkyl group. n represents an integer of 1-8.)

[Invention 8]

A method according to any one of Invention 3 to Invention 7, which is characterized by that, in any one of Invention 3 to Invention 7, a crude product of the fluoroalkanesulfinic acid ammonium salt obtained after the sulfinating reaction is extracted with an organic solvent, and a layer comprising the organic solvent is purified by washing with water.

[Invention 9]

A method according to any one of Invention 3 to Invention 8, which is characterized by that, in any one of Invention 3 to Invention 8, a crude product of the fluoroalkanesulfinic acid ammonium salt obtained after the sulfinating reaction is extracted with an organic solvent, and a layer comprising the organic solvent is purified by washing with a thiosulfuric acid metal salt aqueous solution or sulfurous acid metal salt aqueous solution.

[Invention 10]

A method according to any one of Invention 3 to Invention 9, which is characterized by that, in any one of Invention 3 to Invention 9, a crude product of the fluoroalkanesulfonic acid ammonium salt obtained after the oxidizing reaction is extracted with an organic solvent, and a layer comprising the organic solvent is purified by washing with water.

DETAILED DESCRIPTION

According to the present invention, there is obtained an effect that it is possible to easily produce fluoroalkanesulfonic acid salts, with a good yield in an industrial scale, which are useful as an intermediate for producing a photoacid generator, which is useful as a chemically amplified resist material suitable for a micro-processing technology, particularly photolithography, in the production steps of semiconductor devices and the like, or as an intermediate for producing a solid electrolyte used for fuel cells and the like, by using a carboxylic acid bromofluoroalkyl ester as the raw material. Furthermore, according to the present invention, there is obtained an effect that it is possible to easily produce fluoroalkanesulfonic acid onium salts, which function as a photoacid generator, with a good yield in an industrial scale.

In the following, the present invention is explained more in detail.

[Sulfinic Acid Ammonium Salt]

A fluoroalkanesulfinic acid ammonium salt of the present invention is represented by the following general formula [2].

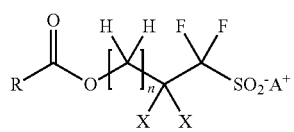

[2]

In the above general formula [2], $A^+$ represents an ammonium ion, and R represents a $C_{1-10}$ straight-chain or branched alkyl group, a $C_{3-20}$ alicyclic organic group, an organic group formed of a $C_{3-20}$ alicyclic organic group and a straight-chain alkylene group, a $C_{3-30}$ monocyclic or polycyclic lactone, or $C_{6-20}$ aryl group. (Herein, hydrogen atoms on the alkyl group, the alicyclic organic group, the organic group formed of the alicyclic organic group and the straight-chain alkylene group, the monocyclic or polycyclic lactone, and the aryl group may partially or completely be replaced with fluorine, hydroxyl group, hydroxycarbonyl group, or a $C_{1-6}$ straight-chain, branched or cyclic alkoxy group. Furthermore, two hydrogen atoms on the same carbon forming the alkyl group, the alicyclic organic group or the organic group formed of the alicyclic organic group and the straight-chain alkylene group may be replaced with one oxygen atom to become a keto group. However, one having a nonconjugated unsaturated moiety (a double bond or triple bond) in the structure is excluded as R. Each X independently represents a group selected from the group consisting of hydrogen atom, fluorine atom, a $C_{1-6}$ alkyl group, and a $C_{1-6}$ fluorine-containing alkyl group. n represents an integer of 1-8.)

Concretely, the ammonium ion represented by $A^+$ can be exemplified by ammonium ion ($NH_4^+$), methylammonium ion ($MeNH_3^+$), dimethylammonium ion ($Me_2NH_2^+$), trimethylammonium ion ($Me_3NH^+$) ethylammonium ion ($EtNH_3^+$), diethylammonium ion ($Et_2NH_2^+$), triethylammonium ion ($Et_3NH^+$), n-propylammonium ion ($n-PrNH_3^+$), di-n-propylammonium ion ($n-Pr_2NH_2^+$), tri-n-propylammonium ion ($n-Pr_3NH^+$), i-propylammonium ion ($i-PrNH_3^+$), di-i-propylammonium ion ($i-Pr_2NH_2^+$), tri-i-propylammonium ion ($i-Pr_3H^+$), n-butylammonium ion ($n-BuNH_3^+$), di-n-butylammonium ion ($n-Bu_2NH_2^+$), tri-n-butylammonium ion ($n-Bu_3NH^+$), sec-butylammonium ion ($sec-BuNH_3^+$), di-sec-butylammonium ion ($sec-Bu_2NH_2^+$), tri-sec-butylammonium ion ($sec-Bu_3NH^+$), tert-butylammonium ion ($t-BuNH_3^+$), di-tert-butylammonium ion ($t-Bu_2NH_2^+$), tri-tert-butylammonium ion ($t-Bu_3NH^+$), diisopropylethylammonium ($i-Pr_2EtNH^+$) phenylammonium ion ($PhNH_3^+$), diphenylammonium ion ($Ph_2NH_2^+$), triphenylammonium ion ($Ph_3NH^+$), tetramethylammonium ion ($Me_4N^+$), tetraethylammonium ion ($Et_4N^+$), trimethylethylammonium ion ($Me_3EtN^+$), tetra-n-propylammonium ion ($n-Pr_4N^+$), tetra-i-propylammonium ion ($i-Pr_4N^+$), tetra-n-butylammonium ion ($n-Bu_4N^+$), or ions having the following structures.

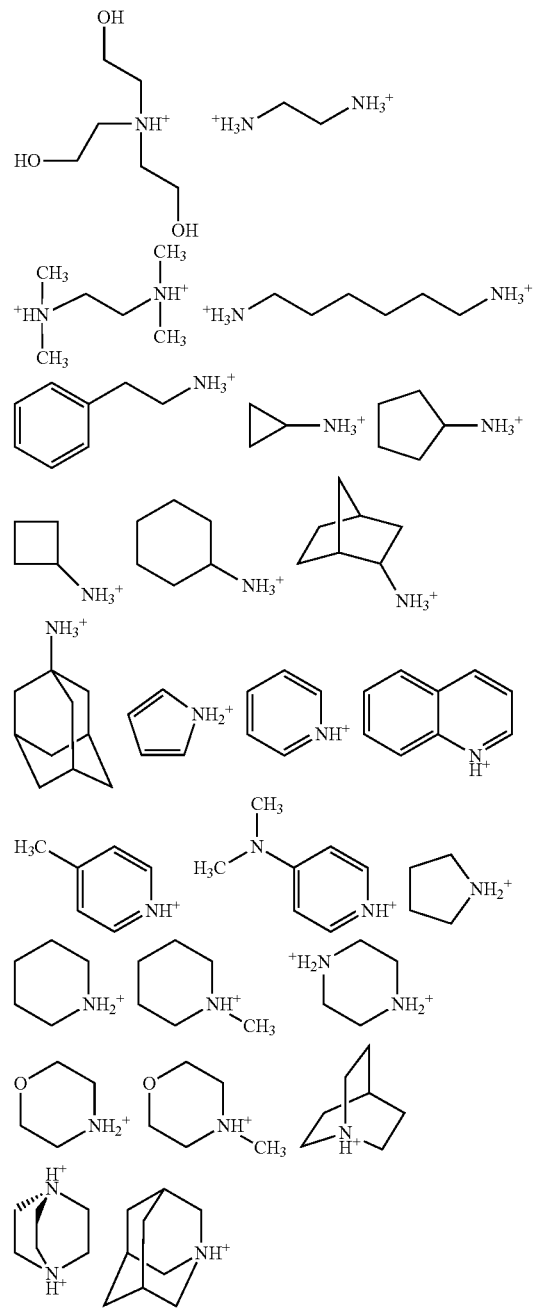

Of these, it is preferable that $A^+$ is an ammonium ion represented by the following general formula [I].

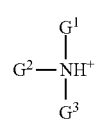

[I]

In the above general formula [I], $G^1$, $G^2$ and $G^3$ mutually independently represent hydrogen atoms, $C_{1-6}$ alkyl groups, $C_{1-6}$ alkoxyalkyl groups, $C_{3-12}$ cycloalkyl groups, optionally substituted phenyl groups, optionally substituted C$_{7-12}$ aralkyl groups, optionally substituted naphthyl groups, optionally substituted C$_{5-10}$ hetero aromatic groups, or a ring optionally containing a hetero atom by at least two of G$^1$, G$^2$ and G$^3$.

Concretely, it can be exemplified by trimethylammonium ion (Me$_3$NH$^+$), triethylammonium ion (Et$_3$NH$^+$), tri-n-propylammonium ion (n-Pr$_3$NH$^+$), tri-i-propylammonium ion (i-Pr$_3$NH$^+$) tri-n-butylammonium ion (n-Bu$_3$NH$^+$), tri-sec-butylammonium ion (sec-Bu$_3$NH$^+$), tri-tert-butylammonium ion (t-Bu$_3$NH$^+$), diisopropylethylammonium ion (i-Pr$_2$EtNH$^+$) triphenylammonium ion (Ph$_3$NH$^+$), or ions having the following structures.

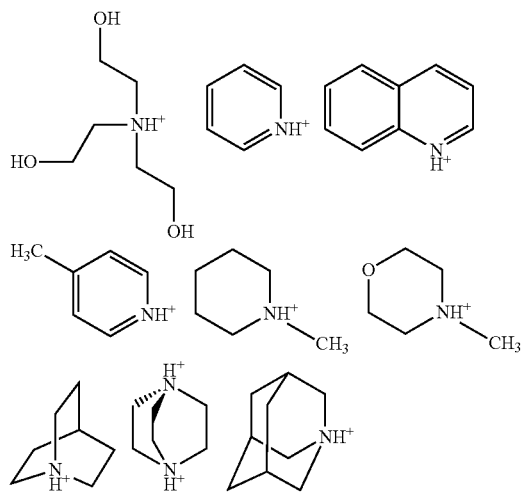

Of these, particularly, trimethylammonium ion (Me$_3$NH$^+$), triethylammonium ion (Et$_3$NH$^+$), and diisopropylethylammonium ion (i-Pr$_2$EtNH$^+$) are preferable.

Then, R is specifically exemplified as follows.

As the C$_{1-10}$ straight-chain or branched alkyl group, it is possible to mention, for example, methyl group, ethyl group, n-propyl group, i-propyl group, n-butyl group, t-butyl group, n-pentyl group, n-hexyl group, n-heptyl group, n-octyl group, n-nonyl group, n-decyl group, etc.

As the C$_{3-20}$ alicyclic organic group, it is possible to mention, for example, cyclopentyl group, cyclohexyl group, adamantyl group, norbornyl group, campholoyl group, cyclopentylmethyl group, cyclopentylethyl group, cyclohexylmethyl group, cyclohexylethyl group, adamantylmethyl group, adamantylethyl group, norbornylmethyl group, norbornylethyl group, campholoylmethyl group, campholoylethyl group, etc.

The organic group formed of a C$_{3-20}$ alicyclic organic group and a straight-chain alkylene group represents an organic group in which an alicyclic organic group and a valence of a straight-chain alkylene group are combined. Specifically, it is possible to mention, for example, cyclopropylmethyl group, cyclobutylmethyl group, cyclopentylmethyl group, cyclohexylmethyl group, bornylmethyl group, norbornylmethyl group, adamantylmethyl group, etc. The number of carbon atoms of this straight-chain alkylene group is not particularly limited, and it is, for example, 1 to 6.

As the C$_{3-30}$ monocyclic or polycyclic lactone, it is possible to mention γ-butyrolactone, γ-valerolactone, angelicalactone, γ-hexylactone, γ-heptalactone, γ-octalactone, γ-nonalactone, 3-methyl-4-octanolide (whiskey lactone), γ-decalactone, γ-undecalactone, γ-dodecalactone, γ-jasmolactone (7-decenolactone), δ-hexylactone, 4,6,6(4,4,6)-trimethyltetrahydropyran-2-one, δ-octalactone, δ-nonalactone, δ-decalactone, δ-2-decenolactone, δ-undecalactone, δ-dodecalactone, δ-tridecalactone, δ-tetradecalactone, lactoscatone, ε-decalactone, ε-dodecalactone, cyclohexyllactone, jasminelactone, cis-jasmonelactone, methyl γ-decalactone or the following.

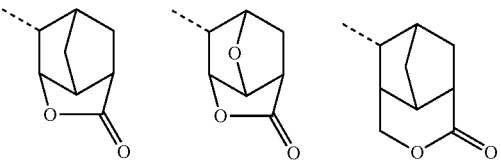

(The dotted line shows the bonding position.)

As the C$_{6-20}$ aryl group, it is possible to mention, for example, phenyl group, o-tolyl group, m-tolyl group, p-tolyl group, p-hydroxyphenyl group, 1-naphthyl group, 1-anthracenyl, benzyl group, etc.

Furthermore, as mentioned above, hydrogen atoms on the alkyl group, the alicyclic organic group, the organic group formed of the alicyclic organic group and the straight-chain alkylene group, the monocyclic or polycyclic lactone, and the aryl group may partially or completely be replaced with fluorine, hydroxyl group, hydroxycarbonyl group, or a C$_{1-6}$ straight-chain, branched or cyclic alkoxy group. Furthermore, two hydrogen atoms on the same carbon forming the alkyl group, the alicyclic organic group or the organic group formed of the alicyclic organic group and the straight-chain alkylene group may be replaced with one oxygen atom to become a keto group. However, one having a nonconjugated unsaturated moiety (a double bond or triple bond) in the structure is excluded as R.

In the above general formula [2], n represents 1 to 8. Specifically, it can be exemplified by compounds having the following structures, and particularly those in which n=2 to 4 are preferable.

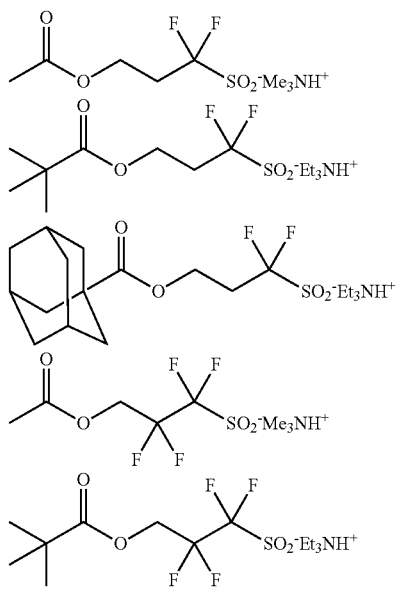

-continued
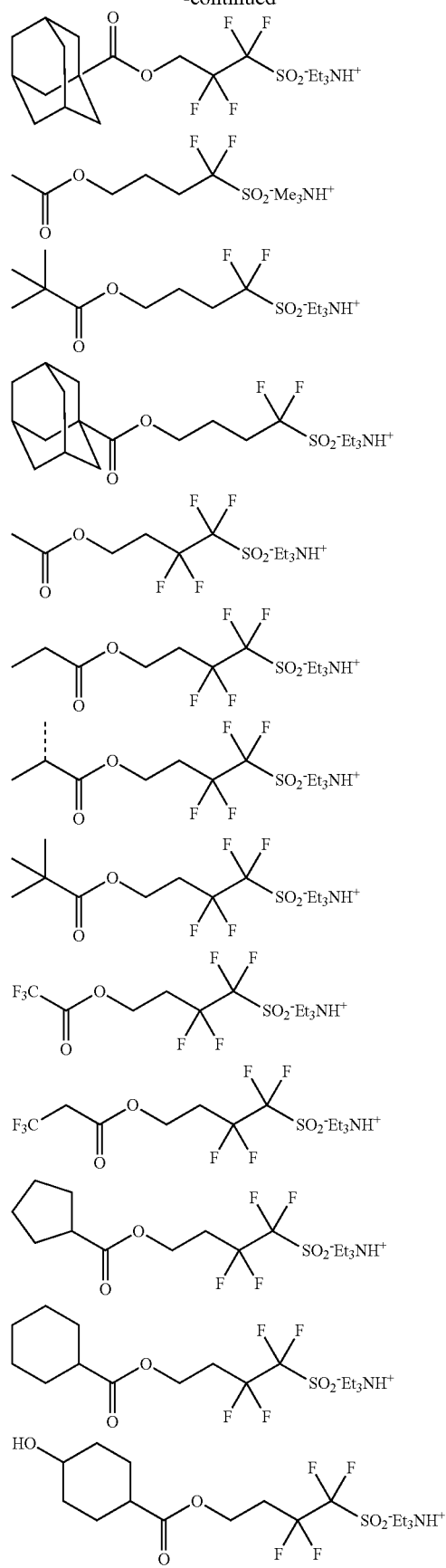
-continued
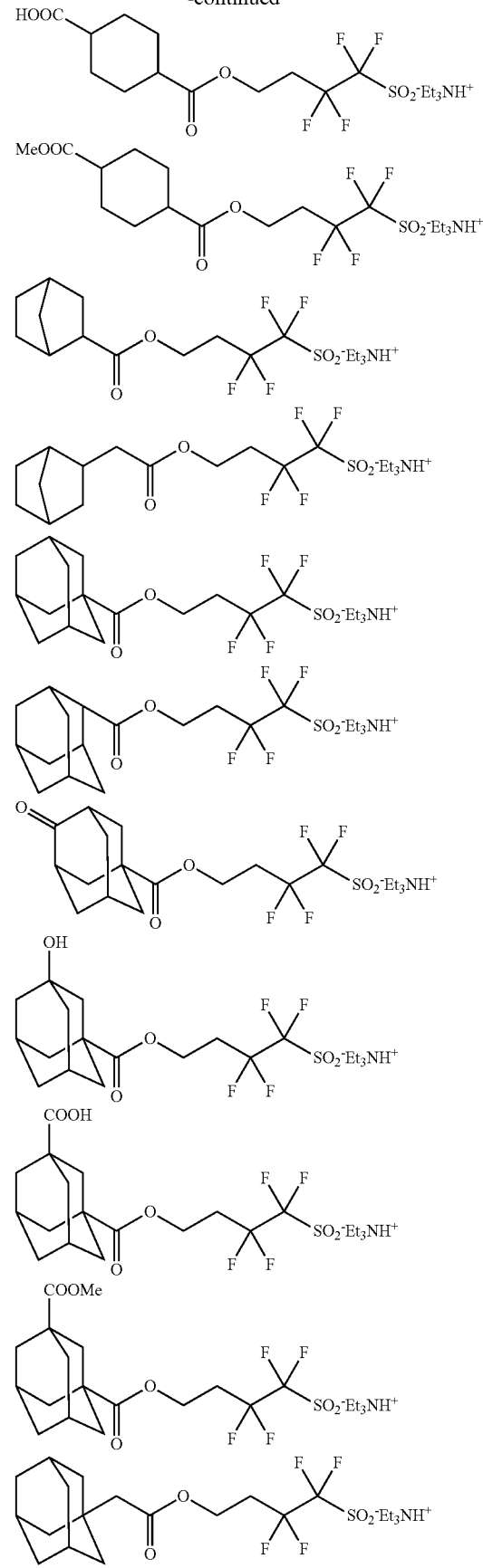

23
-continued
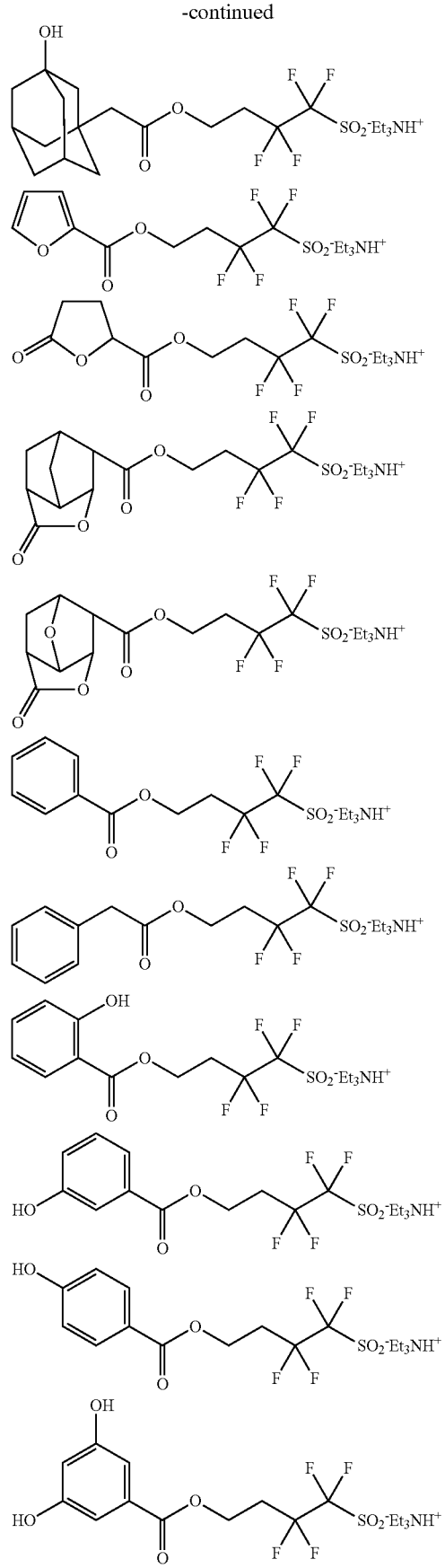
24
-continued
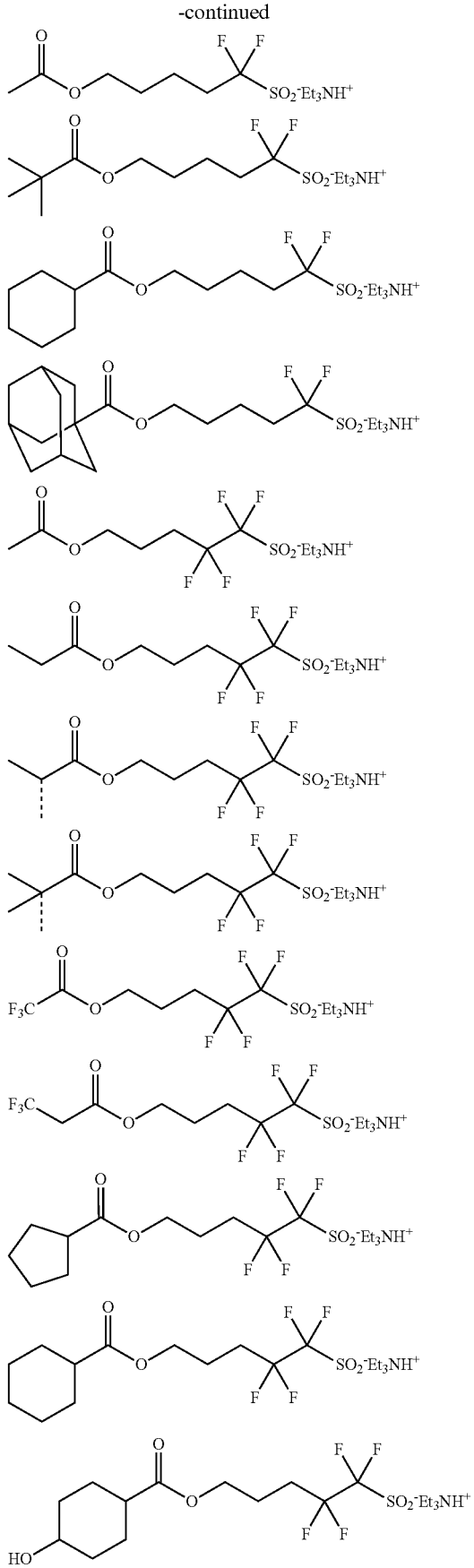

25
-continued
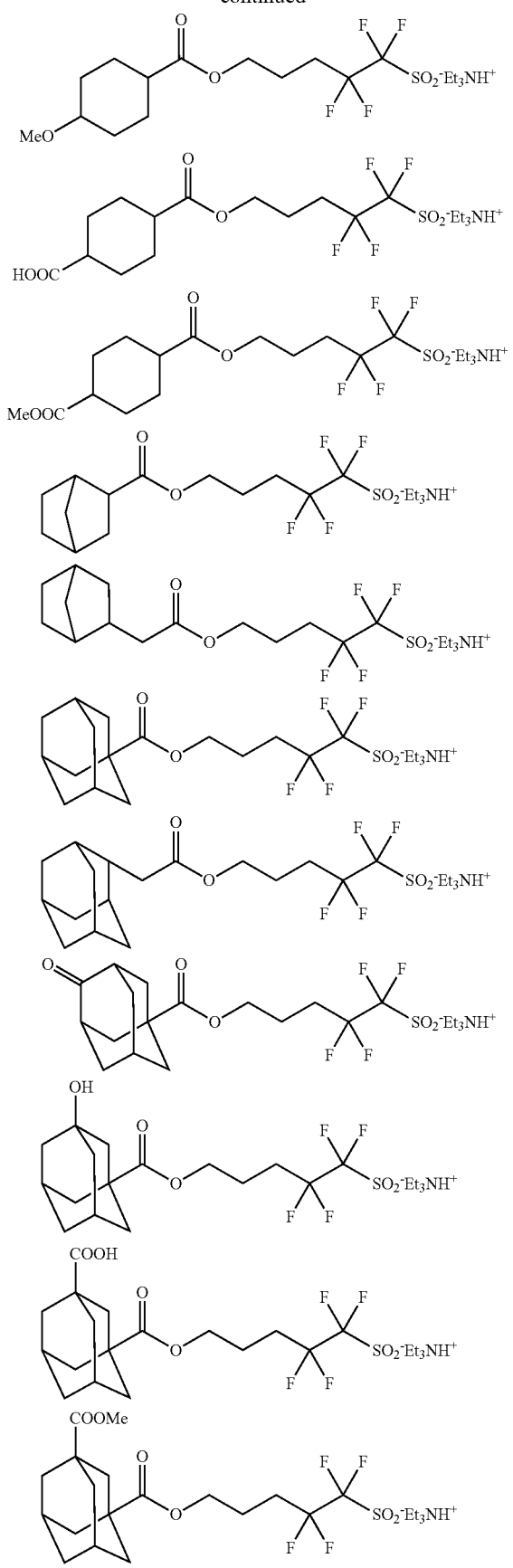
26
-continued
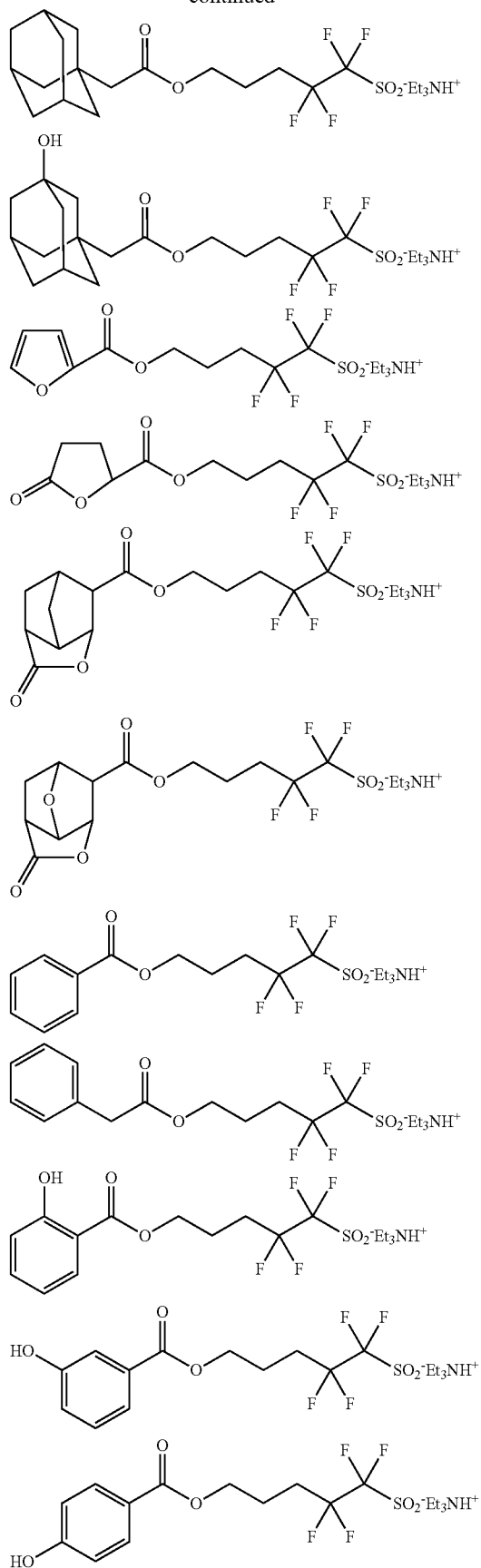

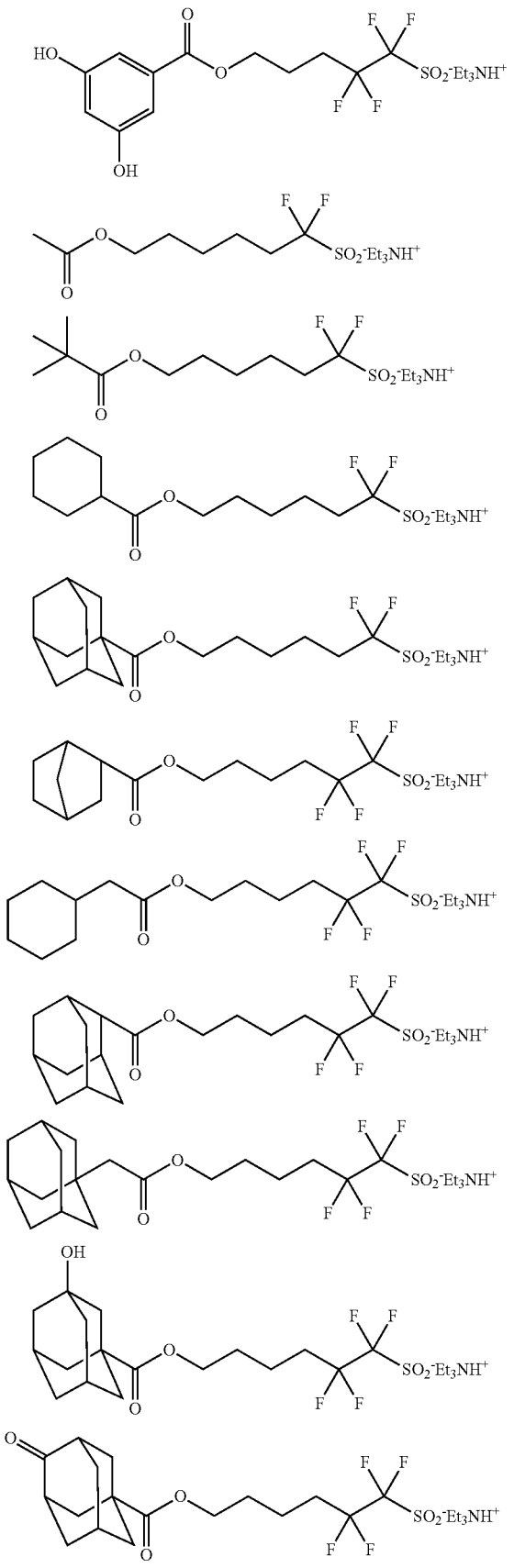
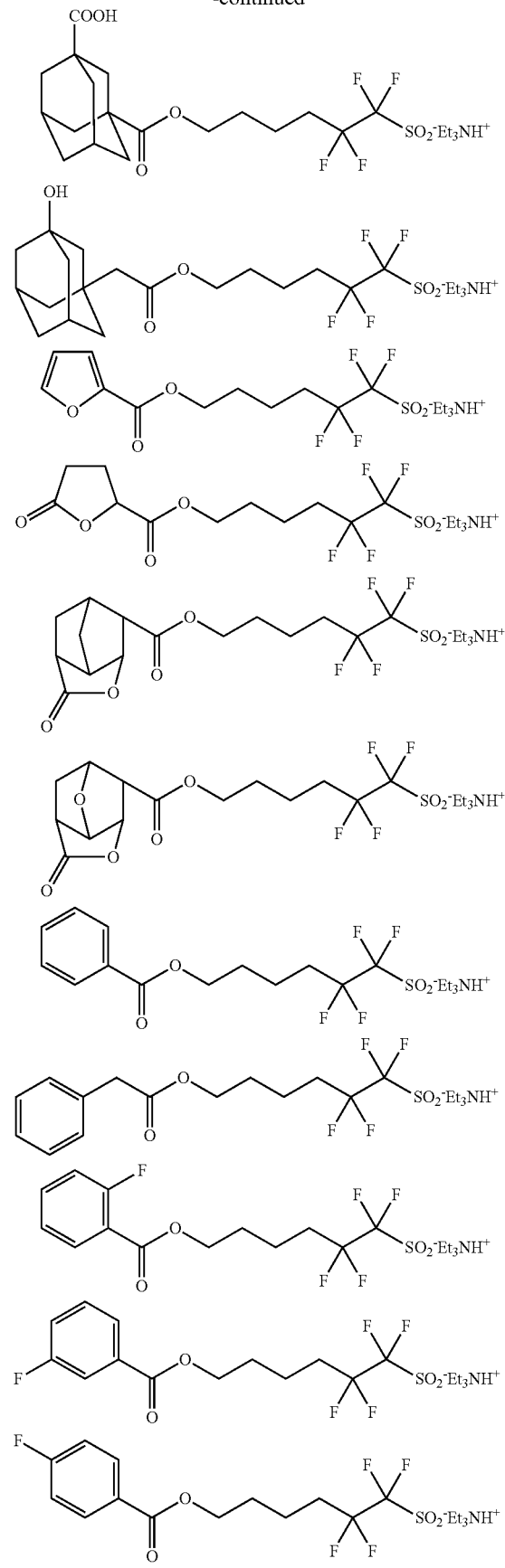

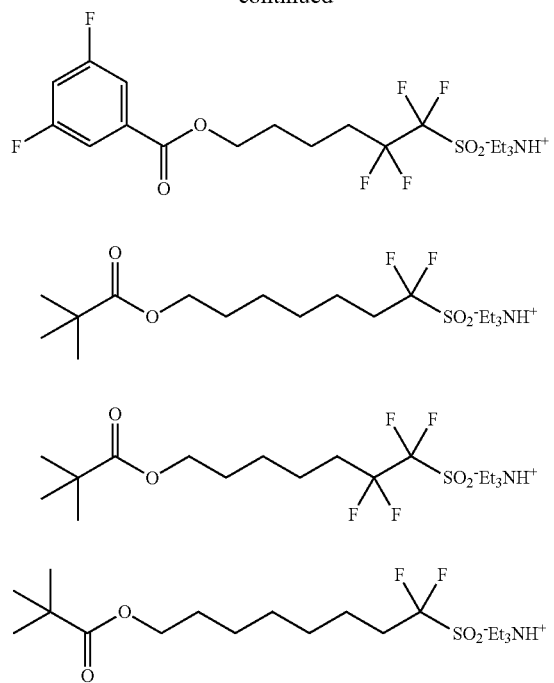
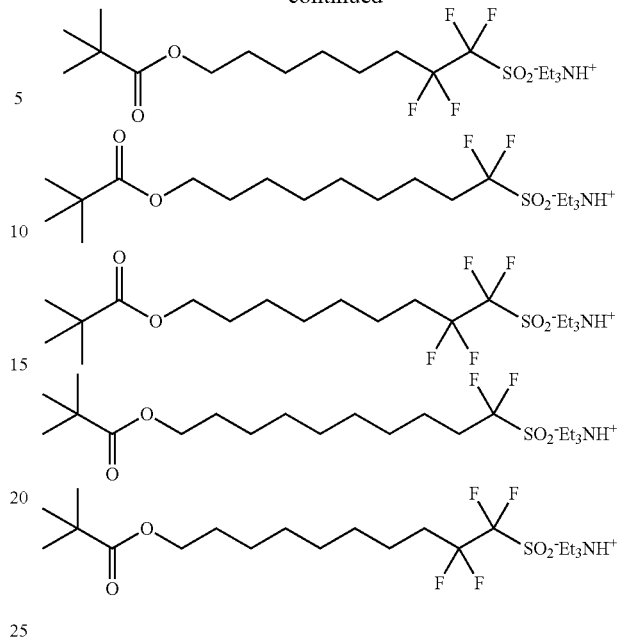
[Summary of the Production Method]
Then, the invention relating to the production method is explained. As shown by the following reaction formula [7],
Reaction formula [7]
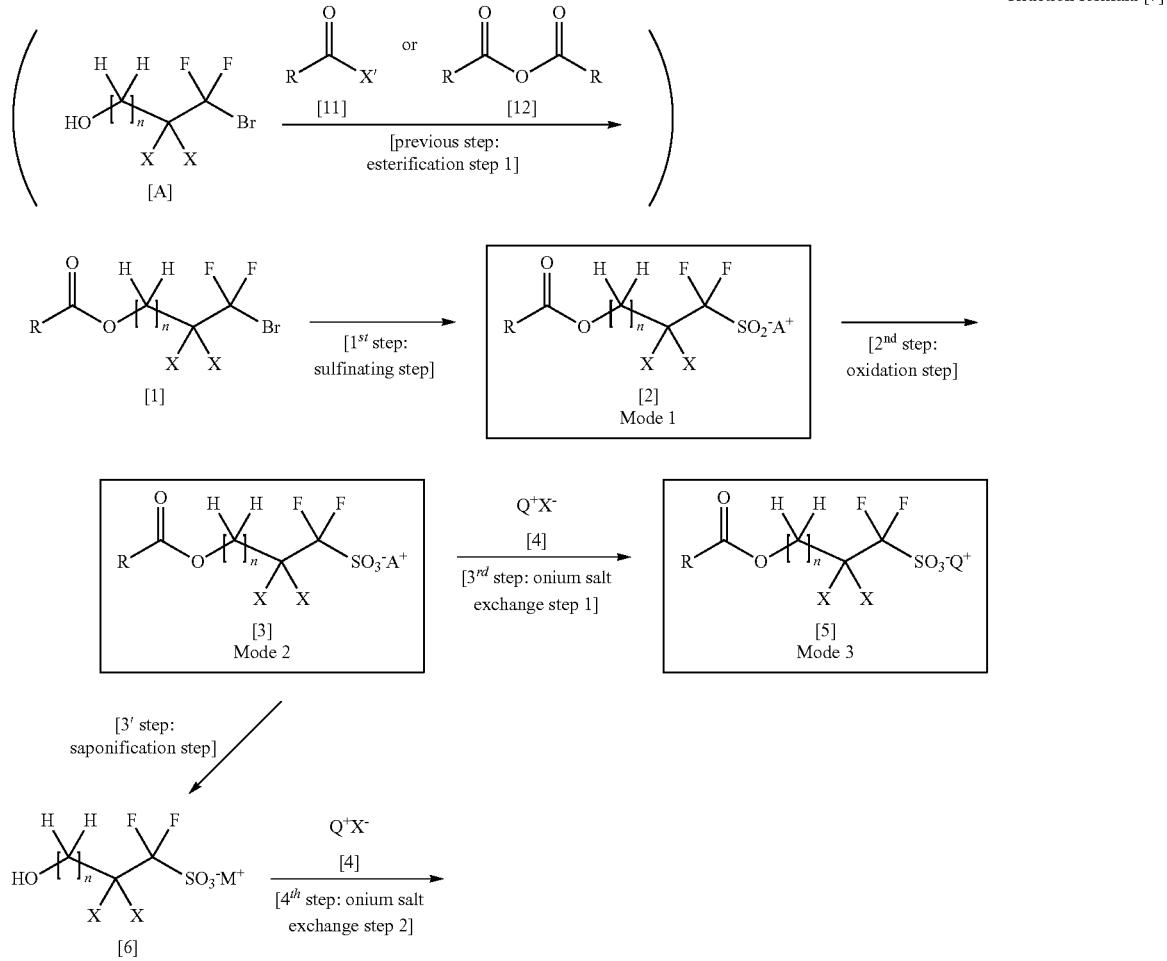

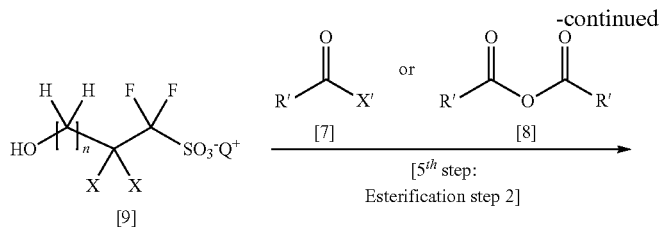 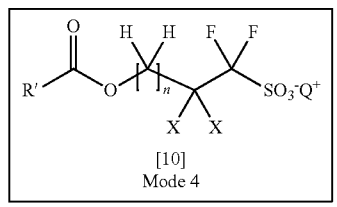

[5th step: Esterification step 2]

Mode 4 the present invention contains three steps of the step (first step: sulfinating step) of obtaining a fluoroalkanesulfinic acid ammonium salt (the target product of Mode 1 of the present invention) represented by general formula [2] by reacting a carboxylic acid bromofluoroalkyl ester represented by general formula [1] with a sulfinating agent in the presence of an amine, the step (second step: oxidation step) of obtaining a fluoroalkanesulfonic acid ammonium salt (the target product of Mode 2 of the present invention) represented by general formula [3] by reacting the obtained fluoroalkanesulfinic acid ammonium salt represented by general formula [2] with an oxidizing agent, and the step (third step: onium salt exchange step 1) of obtaining a fluoroalkanesulfonic acid onium salt (the target product of Mode 3 of the present invention) represented by general formula [5] by subjecting the obtained fluoroalkanesulfonic acid ammonium salt represented by general formula [3] to an onium salt exchange using a monovalent onium salt represented by general formula [4]. By going through this step, it is possible to obtain a fluoroalkanesulfonic acid onium salt that is free from a nonconjugated unsaturated moiety (a double bond or triple bond) as R in general formula [5].

Regarding one having a nonconjugated unsaturated moiety (a double bond or triple bond), it can be obtained by going through three steps of the step (3' step saponification step) of obtaining a hydroxyfluoroalkanesulfonic acid salt represented by general formula [6] by subjecting a fluoroalkanesulfonic acid ammonium salt represented by general formula [3] and obtained by the second step to a saponification, the step (fourth step: onium salt exchange step 2) of producing a hydroxyfluoroalkanesulfonic acid onium salt represented by general formula [9] by subjecting the obtained hydroxyfluoroalkanesulfonic acid salt represented by general formula [6] to an onium salt exchange using a monovalent onium salt represented by general formula [4], and furthermore the step ([fifth step]: esterification step 2) of conducting an esterification by reacting the obtained hydroxyfluoroalkanesulfonic acid onium salt represented by general formula [9] with a carboxylic acid derivative represented by general formula [7] or general formula [8]. Thus, it is also possible to obtain a fluoroalkanesulfonic acid onium salt having a nonconjugated unsaturated moiety (a double bond or triple bond) as R' in general formula [10] by going through the five steps from a carboxylic acid bromofluoroalkyl ester represented by general formula [1].

It is possible to easily produce a carboxylic acid bromofluoroalkyl ester represented by general formula [1] of the starting raw material by going through a step ([the previous step] esterification step 1) of esterifying the corresponding bromofluoro alcohol.

In the following, each step is explained in detail.

[First Step: Sulfinating Step]

Firstly, the first step of the present invention is explained. The first step is a step (sulfinating step) of obtaining a fluoroalkanesulfinic acid ammonium salt by reacting a carboxylic acid bromofluoroalkyl ester represented by general formula [1] with a sulfinating agent in the presence of an organic base.

Firstly, as a sulfinating agent used in the present step, it is possible to use one represented by general formula [16]

$(S^1)_m(M^1)_n \cdot pH_2O$     [16]

(In the above general formula [16], $S^1$ represents $S_2O_4$, $HOCH_2SO_2$, $SO_4$ or $HSO_4$, m and n represent integers, and p represents 0 (zero) or an integer. $M^1$ represents Li, Na, K or $NH_4$.) Specifically, it is exemplified by lithium dithionite, sodium dithionite, potassium dithionite, ammonium dithionite, lithium hydroxymethanesulfinate, sodium hydroxymethanesulfinate, potassium hydroxymethanesulfinate, ammonium hydroxymethanesulfinate, lithium sulfite, sodium sulfite, potassium sulfite, ammonium sulfite, lithium hydrogensulfite, sodium hydrogensulfite, potassium hydrogensulfite, ammonium hydrogensulfite, etc. Of this, sodium dithionite and potassium dithionite are preferable, and sodium dithionite is particularly preferable.

The molar ratio of the sulfinating agent to the carboxylic acid bromofluoroalkyl ester [1] is normally 0.5-10, preferably 0.9-5.0, and particularly preferably it is 1.0-2.0.

The present reaction can be conducted even in the air, but the sulfinating agent may be decomposed by water in the air. Therefore, it is preferable to conduct that in nitrogen or argon atmosphere.

In general, the sulfinating reaction using a sulfinating agent may proceed even if no base is added, but the reaction can be accelerated by adding it. Therefore, generally it is added. As the base to be added, in general, there is used an inorganic base such as sodium carbonate, potassium carbonate, sodium hydrogencarbonate, potassium hydrogencarbonate, or the like. In contrast with this, in the present invention, it is a distinguishing feature to use amine as the base.

The organic base to be used (to be coexistent) in the present step is a free amine obtained by removing a proton ($H^+$) from various ammonium ions that are exemplarily shown as $A^+$ in the above-mentioned formula [2]. It can be exemplified by, for example, ammonia, methylamine, dimethylamine, trimethylamine, ethylamine, diethylamine, triethylamine, n-propylamine, di-n-propylamine, tri-n-propylamine, i-propylamine, di-i-propylamine, tri-i-propylamine, n-butylamine, di-n-butylamine, tri-n-butylamine, sec-butylamine, di-sec-butylamine, tri-sec-butylamine, tert-butylamine, di-tert-butylamine, tri-tert-butylamine, diisopropylethylamine, phenylamine, diphenylamine, triphenylamine, or organic bases having the following structures.

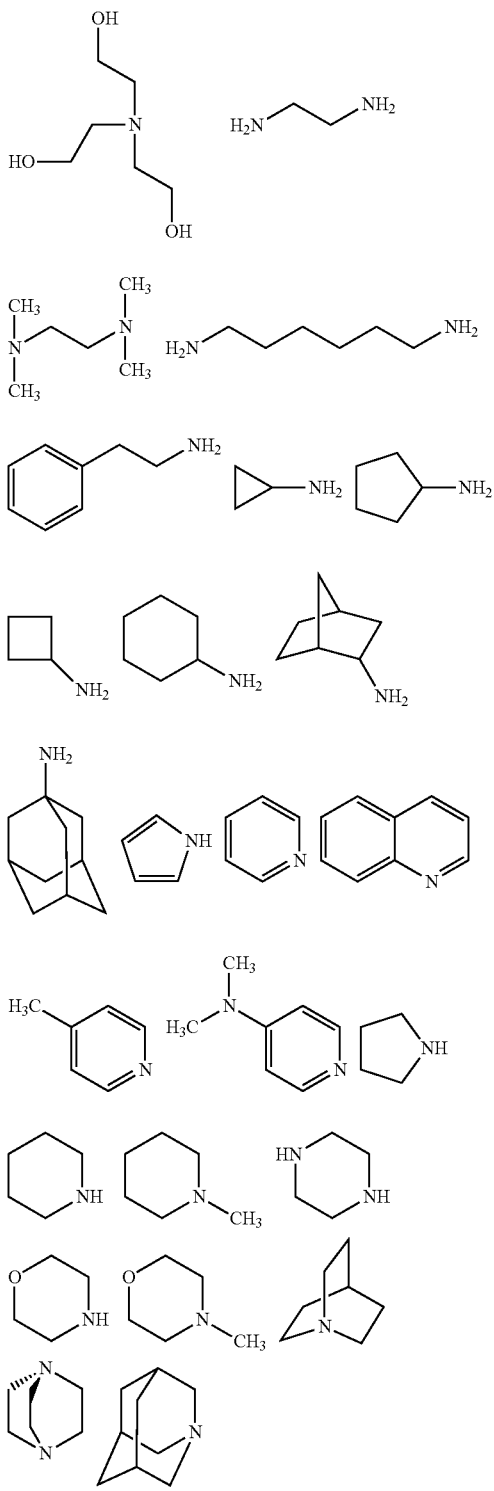

Of these, it is possible to exemplarily mention as preferable organic bases trimethylamine, triethylamine, tri-n-propylamine, tri-i-propylamine, tri-n-butylamine, tri-sec-butylamine, tri-tert-butylamine, diisopropylethylamine, triphenylamine, and organic bases having the following structures.

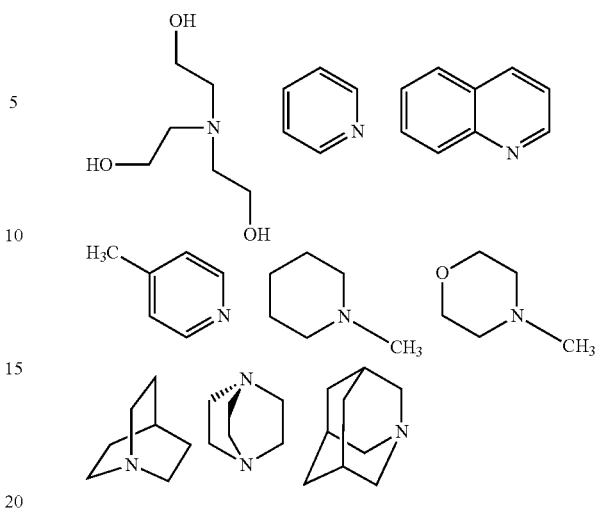

Of these, particularly, trimethylamine, triethylamine and diisopropylethylamine are not only easily available, but also are outstanding in the improvement of reactivity of the sulfinating reaction. Furthermore, fat-solubility of a fluoroalkanesulfinic acid ammonium salt to be obtained is also sufficiently improved. Therefore, they are preferable.

The molar ratio of the organic base to the carboxylic acid bromofluoroalkyl ester [1] is normally 1.0-10.0, preferably 1.1-2.0. If the molar ratio is less than 1.0, a fluoroalkanesulfinic acid metal salt is produced as a by-product by a cation (metal cation such as sodium ion, potassium ion or lithium ion) derived from the sulfinating agent. In this case, not only it becomes difficult in the subsequent steps to conduct a separation between the ammonium salt and the metal salt, but also yield of the target product is lowered. Therefore, it is not preferable. Furthermore, even if the molar ratio exceeds 10.0, no problem occurs. It is, however, economically disadvantageous. Therefore, it is not preferable.

This reaction is conducted preferably in a mixed solvent of an organic solvent and water. As the above organic solvent, solvents having a good compatibility with water are preferable, such as lower alcohols, tetrahydrofuran, N,N-dimethylformamide, N,N-dimethylacetamide, acetonitrile, and dimethylsulfoxide. More preferably, they are methanol, N,N-dimethylacetamide, acetonitrile, dimethylsulfoxide, etc. Particularly preferably, it is acetonitrile.

The proportion of the use of the organic solvent is normally not less than 5 parts by weight, preferably not less than 10 parts by weight, more preferably 20-90 parts by weight, relative to 100 parts by weight of the total of the organic solvent and water.

The reaction temperature is normally 0-200° C., preferably 30-100° C. The reaction time is normally 0.1-12 hours, preferably 0.5-6 hours. Using an analytical apparatus such as thin-layer chromatography (TLC) or nuclear magnetic resonator (NMR), it is preferable to judge the point when the raw material carboxylic acid bromofluoroalkyl ester [1] has been consumed, as the end point of the reaction. Furthermore, in case that the reaction temperature is higher than the boiling point of the organic solvent or water, a pressure-proof vessel such as autoclave is used.

Herein, with respect to the reaction time, in the case of a comparison by using the carboxylic acid bromofluoroalkyl ester [1] having the same structure, the reaction time in the case of using an inorganic base such as sodium carbonate, potassium carbonate, sodium hydrogencarbonate, potassium hydrogencarbonate or the like becomes several times to several tens of times that in the case of using an organic base. Specifically, it takes about 15 hours to 120 hours. In some cases, the reaction is not completed. In such a case, one cannot complete the reaction and cannot obtain the target sulfinated product with a high yield, if one does not conduct an operation of separating the reaction liquid into two layers, discarding the aqueous layer, and then adding again water, the sulfinating agent and the base to resume the reaction, etc. In contrast with this, in the case of using amine as the base, the reaction is markedly accelerated, and in some cases one can complete the reaction in several tens of minutes. Thus, it is one of advantageous effects of using amine as the base in the present invention to be able to markedly shorten the reaction time.

Then, the treatment after the reaction is described. In the first step of the present invention, amine is used as the base. Therefore, fat-solubility of the fluoroalkanesulfinic acid ammonium salt to be obtained is improved. As a result of this, it becomes possible to extract the target sulfinic acid ammonium salt from the reaction liquid (a homogeneous liquid formed of water and an organic solvent having a high compatibility with water, or a liquid that can be separated into two layers, but is formed of an organic layer in which water is dissolved and an aqueous layer in which organic solvent is dissolved) by using an organic solvent that has a low water-solubility or no water-solubility. Such solvent can be exemplified by halogen-series solvents such as chloroform and dichloromethane, ether-series solvents such as diethyl ether, diisopropyl ether and tert-butyl methyl ether, or acetate-series solvents such as ethyl acetate and butyl acetate.

Then, washing this organic layer with water or the like also makes it possible to remove inorganic substances and the like mixed with the organic layer. Particularly problematic is fluorine ions, which are produced in a trace amount as a by-product in the present reaction. Once it has been possible to extract the ammonium salt by using an organic solvent, it becomes possible to remove the remaining fluorine ions by washing or the like (see Example 1-2, Example 2-2 and Comparative Example 1-1).

Furthermore, in the present reaction, bromine is released from the raw material carboxylic acid bromofluoroalkyl ester. Therefore, in the reaction liquid, there exists bromine mark equivalent to the raw material. By conducting the oxidation reaction of the next step while containing this bromine mark, the bromine mark is also oxidized, and a chemical species (probably bromine) having a bromination power is generated and brominates the fluoroalkanesulfinic acid ammonium salt to produce the raw material fluoroalkanesulfinic acid ammonium salt as a by-product. We, however, have made findings that the bromine marks are treated by extracting the fluoroalkanesulfinic acid ammonium salt with a non-water-soluble organic solvent and washing the organic solvent with a sodium thiosulfate aqueous solution or sodium sulfite aqueous solution, and thereby it is possible to suppress the production of carboxylic acid bromofluoroalkyl ester as a by-product in the oxidation reaction of the next step (see Example 1-3, Example 2-3, Comparative Example 2-1 and Comparative Example 2-2).

The molar ratio of the sodium thiosulfate or sodium sulfite to be used to the carboxylic acid bromofluoroalkyl ester [1] is normally 0.1-10.0, preferably 1.0-5.0. The concentration of the sodium thiosulfate aqueous solution or sodium sulfite aqueous solution to be used is normally from 3 weight % to the saturated condition, and 5-25 weight % is preferable.

On the other hand, the fluoroalkanesulfinic acid metal salt obtained by using an inorganic base has a lower fat-solubility and indeed a higher water-solubility, as compared with the ammonium salt. Therefore, an extraction by organic solvent becomes difficult. Even if the extraction is possible, distribution into the aqueous layer is also a lot due to its water-solubility, and it becomes difficult to obtain the target sulfinic acid metal salt with a high yield. Therefore, it becomes necessary to totally concentrate the reaction liquid in order to obtain the sulfinic acid metal salt with a good yield. In general, concentration of water is more difficult than concentration of organic solvent. Furthermore, as mentioned above, fluorine ion is produced as a by-product in the present reaction, although it is a trace amount. If concentration is continued without removing this, it becomes a high concentration gradually and corrodes glassware. Furthermore, as mentioned above, no removal of bromine marks will hinder the subsequent step. Thus, it is another advantageous effect of using an organic base in the present invention to not only improve yield and improve efficiency of the isolation operation but also make it easy to remove inorganic impurities, particularly fluoride ions and bromine mark.

Thus, it is possible to obtain the target sulfinic acid ammonium salt, for example, by conducting an extraction with organic solvent, washing the organic layer with water and a sodium thiosulfate aqueous solution (or a sodium sulfite aqueous solution), etc., and furthermore distilling the solvent out of the organic layer. In some cases, purification is also possible by recrystallization or the like.

[Second Step: Oxidation Step]

Then, the second step of the present invention is explained. The second step is a step (oxidation step) to obtain a fluoroalkanesulfonic acid ammonium salt represented by general formula [3] by reacting the fluoroalkanesulfinic acid ammonium salt [2], which has been obtained by the first step, with an oxidizing agent.

As the oxidizing agent to be used in the present step, it is possible to mention, in addition to hydrogen peroxide, meta-chloroperbenzoic acid, t-butylhydroperoxide, potassium peroxysulfate, potassium permanganate, sodium perborate, sodium metaiodate, chromic acid, sodium dichromate, halogens, iodobenzene dichloride, iodobenzene diacetate, osmium (VIII) oxide, ruthenium (VIII) oxide, sodium hypochlorite, sodium chlorite, oxygen gas, ozone gas, etc. Preferably, they are hydrogen peroxide, meta-chloroperbenzoic acid, t-butylhydroperoxide, etc.

The molar ratio of the oxidizing agent to the fluoroalkanesulfinic acid ammonium salt is normally 0.9-10.0, preferably 1.0-2.0. In case that the raw material sulfinic acid ammonium salt is a crude product and therefore the correct amount by mole is not known, it suffices to add the oxidizing agent to the amount by mole of a carboxylic acid bromofluoroalkyl ester represented by general formula [1], which is prior to the sulfination.

Furthermore, it is also possible to use a transition metal catalyst together with the oxidizing agent. As the transition metal catalyst, it is possible to mention, for example, disodium tungstate, iron (III) chloride, ruthenium (III) chloride, selenium (IV) oxide, etc. Preferably, it is disodium tungstate.

The molar ratio of the transition metal catalyst to the fluoroalkanesulfinic acid ammonium salt is normally 0.0001-1.0, preferably 0.001-0.5, more preferably 0.001-0.1.

Furthermore, in addition to the oxidizing agent and the transition metal catalyst, it is also possible to use a buffer for the purpose of adjusting pH of the reaction liquid. As the buffer, it is possible to mention, for example, disodium hydrogenphosphate, sodium dihydrogenphosphate, dipotassium hydrogenphosphate, potassium dihydrogenphosphate, etc.

The molar ratio of the buffer to the fluoroalkanesulfinic acid ammonium salt is normally 0.01-2.0, preferably 0.03-1.0, more preferably 0.05-0.5.

This reaction is conducted normally in a reaction solvent. As the reaction solvent, water and organic solvents such as lower alcohols, tetrahydrofuran, N,N-dimethylformamide, N,N-dimethylacetamide, acetonitrile, dimethylsulfoxide, acetic acid, trifluoroacetic acid, etc. are preferable. More preferably, they are water, methanol, N,N-dimethylacetamide, acetonitrile, dimethylsulfoxide, etc. Particularly preferably, they are water and methanol.

Furthermore, according to need, it is also possible to use an organic solvent and water together. The proportion of the use of the organic solvent in that case is normally not less than 5 parts by weight, preferably not less than 10 parts by weight, more preferably 20-90 parts by weight, relative to 100 parts by weight of the total of the organic solvent and water. The amount of the use of the reaction solvent to 1 part by weight of the fluoroalkanesulfinic acid ammonium salt is normally 1-100 parts by weight, preferably 2-100 parts by weight, more preferably 5-50 parts by weight.

The reaction temperature is normally 0-100° C., preferably 5-60° C., more preferably 5-40° C. The reaction time is normally 0.1-72 hours, preferably 0.5-24 hours, more preferably 0.5-12 hours. Using an analytical apparatus such as thin-layer chromatography (TLC) or nuclear magnetic resonator (NMR), it is preferable to judge the point when the raw material fluoroalkanesulfinic acid ammonium salt has been consumed, as the end point of the reaction.

Then, the treatment after the reaction is described. In the above-mentioned first step, amine is used as the base. Therefore, fat-solubility of the fluoroalkanesulfinic acid ammonium salt to be obtained is improved. As a result of this, it becomes possible to extract the target sulfonic acid ammonium salt from the reaction liquid (in general, water or methanol is a main component) by using an organic solvent that has a low water-solubility or no water-solubility. Such solvent can be exemplified by halogen-series solvents such as chloroform and dichloromethane, ether-series solvents such as diethyl ether, diisopropyl ether and tert-butyl methyl ether, or acetate-series solvents such as ethyl acetate and butyl acetate.

Then, washing this organic layer with water or the like makes it possible to remove water-soluble impurities containing inorganic salts, which have been mixed with the organic layer, and thereby it is possible to improve purity of the fluoroalkanesulfonic acid ammonium salt to be obtained (see Example 1-3, Example 2-3 and Comparative Example 2-1).

The proportion of the use of water in this case is normally 1-100 parts by weight, preferably 2-100 parts by weight, more preferably 5-50 parts by weight, relative to 1 part by weight of the fluoroalkanesulfinic acid ammonium salt.

The obtained fluoroalkanesulfonic acid ammonium salt can also be purified by recrystallization or the like in some cases.

[Third Step: Onium Salt Exchange Step 1]

Then, the third step of the present invention is explained. The third step is a step (onium salt exchange step 1) for obtaining a fluoroalkanesulfonic acid onium salt represented by general formula [5] by subjecting the fluoroalkanesulfonic acid ammonium salt represented by general formula [3], which has been obtained by the second step, to an onium salt exchange using a monovalent onium salt represented by general formula [4].

$$Q^+X^- \quad [4]$$

The onium cation $Q^+$ contained in general formula [4] represents a sulfonium cation represented by the following general formula (a) or the following general formula (b), or an iodonium cation represented by the following general formula (c).

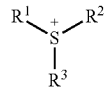
(a)

In the above general formula (a), $R^1$, $R^2$ and $R^3$ mutually independently represent substituted or unsubstituted $C_{1-10}$ straight-chain or branched alkyl groups, alkenyl groups or oxoalkyl groups; or substituted or unsubstituted $C_{6-18}$ aryl groups, aralkyl groups or aryloxoalkyl groups; or any two or more of $R^1$, $R^2$ and $R^3$ may be connected with each other to form a ring together with the sulfur atom in the formula.

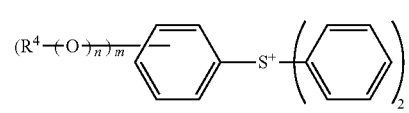
(b)

In the above general formula (b), $R^4$ represents a substituted or unsubstituted $C_{1-20}$ straight-chain, branched or cyclic alkyl group or alkenyl group; or substituted or unsubstituted $C_{6-14}$ aryl group. m represents an integer of 1-5, and n represents 0 (zero) or 1.

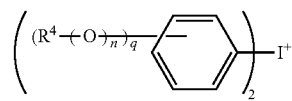
(c)

In the above general formula (c), $R^4$ represents a substituted or unsubstituted $C_{1-20}$ straight-chain, branched or cyclic alkyl group or alkenyl group; or substituted or unsubstituted $C_{6-14}$ aryl group. q represents an integer of 0 (zero) to 5, and n represents 0 (zero) or 1.

In the following, the sulfonium cations represented by general formula (a) and general formula (b) and the iodonium cation represented by general formula (c) are described in detail.

Sulfonium Cation Represented by General Formula (a)

As $R^1$, $R^2$ and $R^3$ in the general formula (a), specifically the followings can be mentioned. As alkyl group, it is possible to mention methyl group, ethyl group, n-propyl group, isopropyl group, cyclopropyl group, n-butyl group, sec-butyl group, isobutyl group, tert-butyl group, n-pentyl group, cyclopentyl group, n-hexyl group, n-heptyl group, n-ethylhexyl group, cyclohexyl group, cycloheptyl group, 4-methylcyclohexyl group, cyclohexylmethyl group, n-octyl group, n-decyl group, 1-adamantyl group, 2-adamantyl group, bicyclo[2.2.1]hepten-2-yl group, 1-adamantanemethyl group, 2-adamantanemethyl group, etc. As alkenyl group, it is possible to mention vinyl group, allyl group, propenyl group, butenyl group, hexenyl group, cyclohexenyl group, etc. As oxoalkyl group, it is possible to mention 2-oxocyclopentyl group, 2-oxocyclohexyl group, 2-oxopropyl group, 2-oxoethyl group, 2-cyclopentyl-2-oxoethyl group, 2-cyclohexyl-2-oxoethyl group, 2-(4-methylcyclohexyl)-2-oxoethyl group, etc. As aryl group, it is possible to mention phenyl group, naphthyl group, thienyl group, etc.; alkoxy phenyl groups such as p-methoxyphenyl group, m-methoxyphenyl group, o-methoxyphenyl group, p-ethoxyphenyl group, p-tert-butoxyphenyl group, m-tert-butoxyphenyl group, etc.; alkylphenyl groups such as 2-methylphenyl group, 3-methylphenyl group, 4-methylphenyl group, ethylphenyl group, etc.; alkylnaphthyl groups such as methylnaphthyl group, ethylnaphthyl group, etc.; dialkylnaphthyl groups such as diethylnaphthyl group, etc.; dialkoxynaphthyl groups such as dimethoxynaphthyl group, diethoxynaphthyl group, etc. As aralkyl group, it is possible to mention benzyl group, 1-phenylethyl group, 2-phenylethyl group, etc. As aryloxoalkyl group, it is possible to mention 2-aryl-2-oxoethyl groups such as 2-phenyl-2-oxoethyl group, 2-(1-naphthyl)-2-oxoethyl group, 2-(2-naphthyl)-2-oxoethyl group, etc. Furthermore, in case that any two or more of $R^1$, $R^2$ and $R^3$ are connected with each other to form a ring through the sulfur atom, it is possible to mention 1,4-butyrene, 3-oxa-1,5-pentyrene, etc. Furthermore, it is possible to mention an aryl group having as the substituent a polymerizable substituent, such as acryloyloxy group, methacryloyloxy group, etc. Specifically, it is possible to mention 4-(acryloyloxy)phenyl group, 4-(methacryloyloxy)phenyl group, 4-vinyloxyphenyl group, 4-vinylphenyl group, etc.

As the sulfonium cation represented by the general formula (a) is shown more specifically, it is possible to mention triphenylsulfonium, (4-tert-butylphenyl)diphenylsulfonium, bis(4-tert-butylphenyl)phenylsulfonium, tris(4-tert-butylphenyl)sulfonium, (3-tert-butylphenyl)diphenylsulfonium, bis(3-tert-butylphenyl)phenylsulfonium, tris(3-tert-butylphenyl)sulfonium, (3,4-di-tert-butylphenyl)diphenylsulfonium, bis(3,4-di-tert-butylphenyl)phenylsulfonium, tris(3,4-di-tert-butylphenyl)sulfonium, (4-tert-butoxyphenyl)diphenylsulfonium, bis(4-tert-butoxyphenyl)phenylsulfonium, tris(4-tert-butoxyphenyl)sulfonium, (3-tert-butoxyphenyl)diphenylsulfonium, bis(3-tert-butoxyphenyl)phenylsulfonium, tris(3-tert-butoxyphenyl)sulfonium, (3,4-di-tert-butoxyphenyl)diphenylsulfonium, bis(3,4-di-tert-butoxyphenyl)phenylsulfonium, tris(3,4-di-tert-butoxyphenyl)sulfonium, diphenyl(4-thiophenoxyphenyl)sulfonium, (4-tert-butoxycarbonylmethyloxyphenyl)diphenylsulfonium, tris(4-tert-butoxycarbonylmethyloxyphenyl)diphenylsulfonium, (4-tert-butoxyphenyl)bis(4-dimethylaminophenyl)sulfonium, tris(4-dimethylaminophenyl)sulfonium, 2-naphthyldiphenylsulfonium, dimethyl(2-naphthyl)sulfonium, (4-hydroxyphenyl)dimethylsulfonium, (4-methoxyphenyl)dimethylsulfonium, trimethylsulfonium, (2-oxocyclohexyl)cyclohexylmethylsulfonium, trinaphthylsulfonium, tribenzylsulfonium, diphenylmethylsulfonium, dimethylphenylsulfonium, 2-oxo-2-phenylethylthiacyclopentanium, diphenyl-2-thienylsulfonium, 4-n-butoxynaphthyl-1-thiacyclopentanium, 2-n-butoxynaphthyl-1-thiacyclopentanium, 4-methoxynaphthyl-1-thiacyclopentanium, 2-methoxynaphthyl-1-thiacyclopentanium, etc. More preferably, it is possible to mention triphenylsulfonium, (4-tert-butylphenyl)diphenylsulfonium, (4-tert-butoxyphenyl)diphenylsulfonium, tris(4-tert-butylphenyl)sulfonium, (4-tert-butoxycarbonylmethyloxyphenyl)diphenylsulfonium, etc.

Furthermore, it is possible to mention 4-(methacryloyloxy)phenyldiphenylsulfonium, 4-(acryloyloxy)phenyldiphenylsulfonium, 4-(methacryloyloxy)phenyldimethylsulfonium, 4-(acryloyloxy)phenyldimethylsulfonium, etc. As to these polymerizable sulfonium cations, it is possible to refer to Japanese Patent Application Publication 4-230645 and Japanese Patent Application Publication 2005-84365, etc.

Sulfonium Cation Represented by General Formula (b)

The position of the substituent of $R^4$—$(O)_n$— group in the general formula (b) is not particularly limited, but 4-position or 3-position of the phenyl group is preferable. More preferably, it is 4-position. Herein, n is 0 (zero) or 1. As $R^4$, specifically it is possible to mention methyl group, ethyl group, n-propyl group, sec-propyl group, cyclopropyl group, n-butyl group, sec-butyl group, iso-butyl group, tert-butyl group, n-pentyl group, cyclopentyl group, n-hexyl group, cyclohexyl group, n-octyl group, n-decyl group, n-dodecyl group, 1-adamantyl group, 2-adamantyl group, bicyclo[2.2.1]hepten-2-yl group, phenyl group, 4-methoxyphenyl group, 4-tert-butylphenyl group, 4-biphenyl group, 1-naphthyl group, 2-naphthyl group, 10-antranyl group, 2-furanyl group, and in the case of n=1 acryloyl group, methacryloyl group, vinyl group, and allyl group.

As specific sulfonium cations, it is possible to mention (4-methylphenyl)diphenylsulfonium, (4-ethylphenyl)diphenylsulfonium, (4-cyclohexylphenyl)diphenylsulfonium, (4-n-hexylphenyl)diphenylsulfonium, (4-n-octyl)phenyldiphenylsulfonium, (4-methoxyphenyl)diphenylsulfonium, (4-ethoxyphenyl)diphenylsulfonium, (4-tert-butoxyphenyl)diphenylsulfonium, (4-cyclohexyloxyphenyl)diphenylsulfonium, (4-trifluoromethylphenyl)diphenylsulfonium, (4-trifluoromethyloxyphenyl)diphenylsulfonium, (4-tert-butoxycarbonylmethyloxyphenyl)diphenylsulfonium, etc.

Iodonium Cation Represented by General Formula (c)

The position of the substituent of $R^4$—$(O)_n$— group in the general formula (c) is not particularly limited, but 4-position or 3-position of the phenyl group is preferable. More preferably, it is 4-position. Herein, n is 0 (zero) or 1. As specific examples of $R^4$, it is possible to mention again the same ones as those of $R^4$ in the general formula (b).

As specific iodonium cations, it is possible to mention diphenyliodonium, bis(4-methylphenyl)iodonium, bis(4-ethylphenyl)iodonium, bis(4-tert-butylphenyl)iodonium, bis(4-(1,1-dimethylpropyl)phenyl)iodonium, (4-methoxyphenyl)phenyliodonium, (4-tert-butoxyphenyl)phenyliodonium, 4-(acryloyloxy)phenylphenyliodonium, 4-(methacryloyloxy)phenylphenyliodonium, etc. In particular, bis(4-tert-butylphenyl)iodonium is preferably used.

Then, as the monovalent anion of $X^-$ in general formula [7], it is possible to mention, for example, $F^-$, $Cl^-$, $Br^-$, $I^-$, $ClO_4^-$, $HSO_4^-$, $H_2PO_4^-$, $BF_4^-$, $PF_6^-$, $SbF_4^-$, aliphatic sulfonic acid anion, aromatic sulfonic acid anion, trifluoromethanesulfonic acid anion, fluorosulfonic acid anion, aliphatic carboxylic acid anion, aromatic carboxylic acid anion, fluorocarboxylic acid anion, trifluoroacetic acid anion, etc. Preferably, they are $Cl^-$, $Br^-$, $HSO_4^-$, $BF_4^-$, aliphatic sulfonic acid ion, etc. More preferably, they are $Cl^-$, $Br^-$ and $HSO_4^-$.

The molar ratio of the monovalent onium salt represented by general formula [4] to the fluoroalkanesulfonic acid ammonium salt [3] is normally 0.5-10.0, preferably 0.8-2.0, more preferably 0.9-1.2.

This reaction is conducted normally in a reaction solvent. As the reaction solvent, water and organic solvents such as lower alcohols, tetrahydrofuran, N,N-dimethylformamide, N,N-dimethylacetamide, acetonitrile, and dimethylsulfoxide are preferable. More preferably, they are water, methanol, N,N-dimethylacetamide, acetonitrile, dimethylsulfoxide, etc. Particularly preferably, it is water.

Furthermore, according to need, it is possible to use water and an organic solvent together. The proportion of the use of the organic solvent in this case is normally not less than 5 parts by weight, preferably not less than 10 parts by weight, more preferably 20-90 parts by weight, relative to 100 parts by weight of the total of water and the organic solvent. The amount of the use of the reaction solvent is normally 1-100, preferably 2-100 parts by weight, more preferably 5-50 parts by weight, relative to 1 part by weight of the counter ion exchange precursor.

The reaction temperature is normally 0-80° C., preferably 5-30° C. The reaction time is normally 10 minutes to 16 hours, preferably 30 minutes to 6 hours. Using an analytical apparatus such as thin-layer chromatography (TLC) or nuclear magnetic resonator (NMR), it is preferable to judge the point when the raw material fluoroalkanesulfonic acid ammonium salt [3] has been consumed, as the end point of the reaction.

According to need, the thus obtained fluoroalkanesulfonic acid onium salt represented by general formula [5] can be purified by washing with an organic solvent or extraction. As the organic solvent, organic solvents immiscible with water, for example, esters such as ethyl acetate and n-butyl acetate, ethers such as diethyl ether, and alkyl halides such as methylene chloride and chloroform are preferable.

By the above-mentioned method, it is possible to obtain a fluoroalkanesulfonic acid onium salt that is free from a nonconjugated unsaturated moiety (a double bond or triple bond) as the substituent of acyl group, in its structure. The present compound can be used as a photoacid generator used for chemically-amplified resist materials. With respect to one having a nonconjugated unsaturated moiety (a double bond or triple bond) as the substituent of acyl group, in its structure, it is difficult to produce that by the above steps. Therefore, it is necessary to further conduct the following steps.

[3' Step: Saponification Step]

Then, 3' step of the present invention is explained. 3' step is a step (saponification step) for obtaining a hydroxyfluoroalkanesulfonic acid salt represented by general formula [6] by subjecting the fluoroalkanesulfonic acid ammonium salt represented by general formula [3], which has been obtained by the second step, to saponification (a hydrolysis in the presence of a basic substance).

As the method for conducting saponification of the fluoroalkanesulfonic acid ammonium salt represented by general formula [3], it is possible to use any of the saponification methods that have become publicly known up to now. There is no particular limitation. The following method can be shown as an example.

In general, saponification reaction is conducted in the presence of a base catalyst. As the base, one or more kinds of alkali-metal hydroxides, bicarbonates and carbonates, ammonia, and amine are included. The alkali metal compound is exemplified by sodium hydroxide, potassium hydroxide, lithium hydroxide, sodium hydrogencarbonate, potassium hydrogencarbonate, sodium carbonate, and potassium carbonate. As the amine, there are shown methylamine, dimethylamine, trimethylamine, ethylamine, diethylamine, triethylamine, propylamine, dipropylamine, tripropylamine, butylamine, dibutylamine, tributylamine, cyclohexylamine, benzylamine, morpholine, pyrrole, pyrrolidine, pyridine, ethanolamine, diethanolamine, triethanolamine, N,N-dimethylaminoethanol, N,N-diethylaminoethanol, ethylene diamine, diethylenetriamine, triethylenetetramine, 1,2-propylenediamine, dipropylenetriamine and tripropylenetetramine, and quaternary ammonium hydroxide salts of these.

Since the raw material is an ammonium salt, the counter cation $M^+$ remains ammonium ion ($A^+$) by using in the present step the same amine as that used when conducting the sulfinating step of the first step. However, in the case of using in the present step a base different from that used when conducting the sulfinating step of the first step, the counter cation $M^+$ changes as follows, depending on the strength of the base to be used.

The raw material fluoroalkanesulfonic acid ammonium salt is in form a salt formed from a fluoroalkanesulfonic acid as a superstrong acid and an amine as a weak base. Therefore, in the case of using a base, which is stronger than the amine used upon conducting the sulfinating step of the first step, in one equivalent or more relative to the fluoroalkanesulfonic acid ammonium salt, $M^+$ becomes a cation derived from the base used in the present step. In the case of using it in one equivalent or less, $M^+$ becomes a mixture of an ammonium cation derived from the raw material and a cation derived from the base used in the present step.

In the case of using a base that is weaker than the amine used in the sulfinating step, even if using it in one equivalent or more, or even if using it in one equivalent or less, in theory, ammonium cation derived from the raw material has no change. In reality, however, there is a possibility that it is replaced with a cation derived from the base used in the present step by the effect of affinity between cation derived from the base used in the present step and the difluoroalkanesulfonate anion, resulting in complication.

Of the bases exemplarily shown above, sodium hydroxide, potassium hydroxide, lithium hydroxide, sodium hydrogencarbonate, potassium hydrogencarbonate, sodium carbonate, and potassium carbonate, which are alkali metal compounds, are preferable. Sodium hydroxide and potassium hydroxide, which are alkali metal hydroxides, are particularly preferable. Since these alkali metal hydroxides are bases stronger than amine, the cation (Mt) to be generated becomes one derived from these alkali metal hydroxides.

The molar ratio of the base to the fluoroalkanesulfonic acid ammonium salt [3] is normally 0.01-10.0, preferably 1.0-5.0, more preferably 1.0-3.0. Even at a molar ratio of 1.0 or less, the saponification reaction itself proceeds. In the case of using in the present saponification reaction a base different from the base derived from the raw material ammonium salt, as mentioned above, the hydroxy product to be generated becomes a mixture of different bases. Therefore, it is preferable to use the base at a molar ratio of 1.0 or more.

This reaction is conducted normally in the presence of water. The molar ratio of water to the fluoroalkanesulfonic acid ammonium salt [3] is normally 1 or more, and there is no upper limitation. However, the efficiency becomes low by using too much amount of water. 100 or less is preferable, and more preferably it is 50 or less.

Furthermore, according to need, it is possible to use water and organic solvent together. There is no particular limitation on the organic solvent used therewith. Organic solvents capable of extracting the hydroxyfluoroalkanesulfonic acid salt represented by general formula [6] from the aqueous layer, organic solvents immiscible with water, for example, esters such as ethyl acetate and n-butyl acetate, ethers such as diethyl ether, and alkyl halides such as methylene chloride and chloroform, are preferable.

The proportion of the use of the organic solvent in this case is normally 5 parts by weight or more, preferably 10 parts by weight or more, more preferably 20-90 parts by weight, relative to 100 parts by weight of the total of water and the organic solvent.

The reaction temperature is normally 0-100° C., preferably 5-80° C. The reaction time is normally 10 minutes to 16 hours, preferably 30 minutes to 6 hours. Using an analytical apparatus such as thin-layer chromatography (TLC) or nuclear magnetic resonator (NMR), it is preferable to judge the point when the raw material fluoroalkanesulfonic acid ammonium salt [3] has been consumed, as the end point of the reaction.

According to need, the thus obtained hydroxyfluoroalkanesulfonic acid salt represented by general formula [6] can be extracted with an organic solvent or purified by recrystallization.

[Fourth Step: Onium Salt Exchange Step 2]

Then, the fourth step of the present invention is explained. The fourth step is a step (onium salt exchange step 2) for obtaining a hydroxyfluoroalkane sulfonic acid onium salt represented by general formula [9] by subjecting a hydroxyfluoroalkanesulfonic acid salt represented by general formula [6], which has been obtained by the 3' step, to an onium salt exchange using a monovalent salt represented by general formula [4]. The present step can be conducted to be similar to the above-mentioned third step (onium salt exchange step 1).

[Fifth Step: Esterification Step 2]

Then, the fifth step of the present invention is explained. The fifth step is a step for producing a fluoroalkanesulfonic acid onium salt represented by general formula [10] by reacting a hydroxyfluoroalkanesulfonic acid onium salt represented by general formula [9], which has been obtained by the fourth step, with a carboxylic acid derivative represented by general formula [7] or general formula [8] to conduct an esterification.

In general formula [7] or general formula [8], R' represents a $C_{1-10}$ straight-chain or branched alkyl group, a $C_{1-10}$ straight-chain or branched alkenyl group having a polymerizable double bond at an end portion at least, a $C_{3-20}$ alicyclic organic group, an organic group formed of a $C_{3-20}$ alicyclic organic group and a straight-chain alkylene group, a $C_{3-30}$ monocyclic or polycyclic lactone, or a $C_{6-20}$ aryl group (Herein, hydrogen atoms on the alkyl group, the alkenyl group, the alicyclic organic group, the organic group formed of the alicyclic organic group and the straight-chain alkylene group, the monocyclic or polycyclic lactone, and the aryl group may partially or entirely be replaced with fluorine, hydroxyl group, hydroxycarbonyl group, or $C_{1-6}$ straight-chain, branched or cyclic alkoxy group. Furthermore, two hydrogen atoms on the same carbon constituting the alkyl group, the alkenyl group, the alicyclic organic group, or the organic group formed of the alicyclic organic group and the straight-chain alkylene group may be replaced with a single oxygen atom to make a keto group. Furthermore, one of the hydrogen atoms on the alkyl group may be replaced with 2-acryloyloxy group or 2-methacryloyloxy group. Each X independently represents a group selected from the group consisting of hydrogen atom, fluorine atom, a $C_{1-6}$ alkyl group, and $C_{1-6}$ fluorine-containing alkyl group. n represents an integer of 1-8.)

R is specifically exemplified as follows.

As the $C_{1-10}$ straight-chain or branched alkyl group, it is possible to mention, for example, methyl group, ethyl group, n-propyl group, i-propyl group, n-butyl group, t-butyl group, n-pentyl group, n-hexyl group, n-heptyl group, n-octyl group, n-nonyl group, n-decyl group, etc.

As the $C_{1-10}$ straight-chain or branched alkenyl group having a polymerizable double bond at an end portion at least, it is possible to mention, for example, vinyl group, 1-methylethenyl group, allyl group, 3-butenyl group, 1-methylallyl group, 2-methylallyl group, 4-pentenyl group, 5-hexenyl group, etc.

As the $C_{3-20}$ alicyclic organic group, it is possible to mention, for example, cyclopentyl group, cyclohexyl group, adamantyl group, norbornyl group, campholoyl group, cyclopentylmethyl group, cyclopentylethyl group, cyclohexylmethyl group, cyclohexylethyl group, adamantylmethyl group, adamantylethyl group, norbornylmethyl group, norbornylethyl group, campholoylmethyl group, campholoylethyl group, etc.

The organic group formed of a $C_{3-20}$ alicyclic organic group and a straight-chain alkylene group represents an organic group in which an alicyclic organic group and a valence of a straight-chain alkylene group are combined. Specifically, it is possible to mention, for example, cyclopropylmethyl group, cyclobutylmethyl group, cyclopentylmethyl group, cyclohexylmethyl group, bornylmethyl group, norbornylmethyl group, adamantylmethyl group, etc. The number of carbon atoms of this straight-chain alkylene group is not particularly limited, and it is, for example, 1 to 6.

As the $C_{3-30}$ monocyclic or polycyclic lactone, it is possible to mention γ-butyrolactone, γ-valerolactone, angelicalactone, γ-hexylactone, γ-heptalactone, γ-octalactone, γ-nonalactone, 3-methyl-4-octanolide (whiskey lactone), γ-decalactone, γ-undecalactone, γ-dodecalactone, γ-jasmolactone (7-decenolactone), δ-hexylactone, 4,6,6(4,4,6)-trimethyltetrahydropyran-2-one, δ-octalactone, δ-nonalactone, δ-decalactone, δ-2-decenolactone, δ-undecalactone, δ-dodecalactone, δ-tridecalactone, δ-tetradecalactone, lactoscatone, ε-decalactone, ε-dodecalactone, cyclohexyllactone, jasminelactone, cis-jasmonelactone, methyl γ-decalactone or the following.

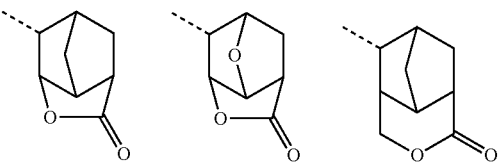

(The dotted line shows the bonding position.)

As the $C_{6-20}$ aryl group, it is possible to mention, for example, phenyl group, o-tolyl group, m-tolyl group, p-tolyl group, p-hydroxyphenyl group, 1-naphthyl group, 1-anthracenyl group, benzyl group, etc.

Furthermore, as mentioned above, hydrogen atoms on the alkyl group, the alkenyl group, the alicyclic organic group, the organic group formed of the alicyclic organic group and the straight-chain alkylene group, the monocyclic or polycyclic lactone, and the aryl group may partially or completely be replaced with fluorine, hydroxyl group, hydroxycarbonyl group, or a $C_{1-6}$ straight-chain, branched or cyclic alkoxy group. Furthermore, two hydrogen atoms on the same carbon forming the alkyl group, the alkenyl group, the alicyclic organic group or the organic group formed of the alicyclic organic group and the straight-chain alkylene group may be replaced with one oxygen atom to become a keto group. Furthermore, one of hydrogen atoms on the alkyl group may be replaced with 2-acryloyloxy group or 2-methacryloyloxy group.

As mentioned above, it is a distinguishing feature to be able to use a nonconjugated unsaturated moiety (a double bond or triple bond), that is, a polymerizable acyl group.

The esterification method can be exemplified by a method (Fisher esterification) in which a carboxylic acid represented by general formula [7] (X'=OH) and the hydroxyfluoroalkanesulfonic acid onium salt [9] are subjected to a dehydration-condensation in the presence of acid catalyst, a method in which a carboxylic halide represented by general formula [7] (X'=Cl, Br, I, F) or a carboxylic anhydride represented by general formula [8] is reacted with the hydroxyfluoroalkanesulfonic acid onium salt [9], etc.

In the case of using a carboxylic acid represented by general formula [7] (X'=OH), there is no particular limitation on the amount of the use of the carboxylic acid represented by general formula [7], which is made to act on the hydroxyfluoroalkanesulfonic acid onium salt [9]. Normally, it is 0.1-5 moles, preferably 0.2-3 moles, more preferably 0.5-2 moles, relative to 1 mole of the hydroxyfluoroalkanesulfonic acid onium salt [9]. It is particularly preferable that the amount of the use of the carboxylic acid is 0.8-1.5 moles.

In the reaction, normally, there is used an aprotic solvent such as dichloroethane, toluene, ethylbenzene, monochlorobenzene, acetonitrile, N,N-dimethylformamide, etc. These solvents may be used singly, or at least two kinds may be used together.

The reaction temperature is not particularly limited. Normally, it is a range of 0-200° C., preferably 20-180° C., more preferably 50-150° C. It is preferable to conduct the reaction with stirring.

The reaction time depends on the reaction temperature, too. Normally, it is several minutes to 100 hours, preferably 30 minutes to 50 hours, more preferably 1-20 hours. Using an analytical apparatus such as nuclear magnetic resonator (NMR), it is preferable to judge the point when the raw material hydroxyfluoroalkanesulfonic acid onium salt [9] has been consumed, as the end point of the reaction.

In the present reaction, normally, there is added as the acid catalyst an organic acid such as p-toluenesulfonic acid and/or an inorganic acid such as sulfuric acid. Alternatively, as the dehydrating agent, it is optional to add 1,1'-carbonyl diimidazole, N,N'-dicyclohexylcarbodiimide, etc. The amount of the use of such acid catalyst is not particularly limited. It is 0.0001-10 moles, preferably 0.001-5 moles, more preferably 0.01-1.5 moles, relative to 1 mole of the hydroxyfluoroalkanesulfonic acid onium salt [9].

If the esterification reaction using an acid catalyst is conducted with dehydration by using a Dean-Stark apparatus or the like, the reaction time tends to be shortened. Therefore, that is preferable.

After terminating the reaction, it is possible to obtain a fluoroalkanesulfonic acid onium salt represented by general formula [10] by a normal measure such as extraction, distillation, recrystallization, etc. Furthermore, according to need, it can also be purified by column chromatography, recrystallization, etc.

On the other hand, in the case of using a carboxylic halide represented by general formula [7] (X'=Cl, Br, I, F) or a carboxylic anhydride represented by general formula [8], there is no particular limitation on the amount of the use of the carboxylic halide represented by general formula [7] or the carboxylic anhydride represented by general formula [8], which is made to act on the hydroxyfluoroalkanesulfonic acid onium salt [9]. Normally, it is 0.1-5 moles, preferably 0.2-3 moles, more preferably 0.5-2 moles, relative to 1 mole of the hydroxyfluoroalkanesulfonic acid onium salt [9]. It is particularly preferable that the amount of the use of the carboxylic halide or the carboxylic anhydride is 0.8-1.5 moles.

The reaction may be conducted with no solvent, or may be conducted in a solvent inert to the reaction. Such solvent is not particularly limited, so long as it is a reaction-inert solvent.

The hydroxyfluoroalkanesulfonic acid onium salt [9] is hardly dissolved in hydrocarbon-series, non-polar solvents such as n-hexane, benzene or toluene, etc. Therefore, they are not preferable as a solvent to be used in the present step. It is preferable to use water, ketone-series solvents such as acetone, methyl ethyl ketone or methyl isobutyl ketone, etc., ester-series solvents such as ethyl acetate or butyl acetate, etc., ether-series solvents such as diethyl ether, diethylene glycol dimethyl ether, tetrahydrofuran or dioxane, etc., halogen-series solvents such as dichloromethane, chloroform, carbon tetrachloride, 1,2-dichloroethane, tetrachloroethylene, chlorobenzene, orthochlorobenzene, etc., and polar solvents such as acetonitrile, N,N-dimethylformamide, N,N-dimethylimidazolidinone, dimethylsulfoxide, sulfolane, etc. These solvents may be used singly, or at least two kinds may be used together.

The reaction temperature is not particularly limited. Normally, it is a range of −78 to 150° C., preferably −20 to 120° C., more preferably 0 to 100° C.

The reaction time depends on the reaction temperature, too. Normally, it is several minutes to 100 hours, preferably 30 minutes to 50 hours, more preferably 1-20 hours. Using an analytical apparatus such as nuclear magnetic resonator (NMR), it is preferable to judge the point when the raw material hydroxyfluoroalkanesulfonic acid onium salt [9] has been consumed, as the end point of the reaction.

In the case of using a carboxylic halide represented by general formula [7], it may be conducted under no catalyst while removing a hydrogen halide (e.g., hydrogen chloride, etc.) produced as a by-product, out of the reaction system, or may be conducted by using a dehydrohalogenation agent (acid acceptor). In the case of using a carboxylic anhydride represented by general formula [8], it may be conducted by using an acid acceptor for capturing an acid produced as a by-product.

As the acid acceptor, it is exemplified by, for example, organic bases such as triethylamine, pyridine, picoline, dimethylaniline, diethylaniline, 1,4-diazabicyclo[2.2.2]octane (DABCO), and 1,8-diazabicyclo[5.4.0]undec-7-ene (DBU), or inorganic bases such as sodium hydrogencarbonate, sodium carbonate, potassium carbonate, lithium carbonate, sodium hydroxide, potassium hydroxide, calcium hydroxide, and magnesium hydroxide. The amount of the use of such acid acceptor is not particularly limited. Relative to 1 mole of the hydroxyfluoroalkanesulfonic acid onium salt [9], it is 0.05-10 moles, preferably 0.1-5 moles, more preferably 0.5-3 moles.

After terminating the reaction, it is possible to obtain a fluoroalkanesulfonic acid onium salt represented by general formula [10] by a normal measure such as extraction, recrystallization, etc. Furthermore, according to need, it can also be purified by column chromatography, recrystallization, etc.

By the way, it is also possible to reverse the order of the fourth step and the fifth step of the present invention.

Reaction formula [8]

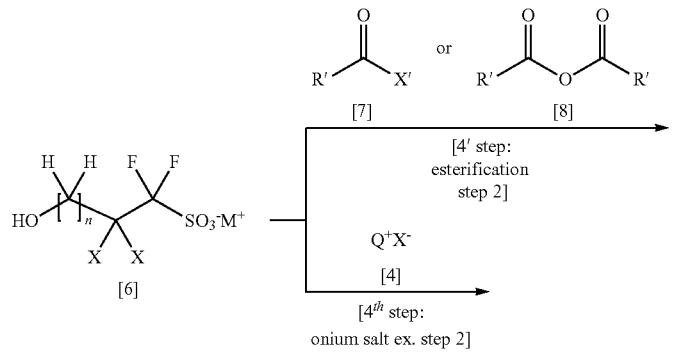

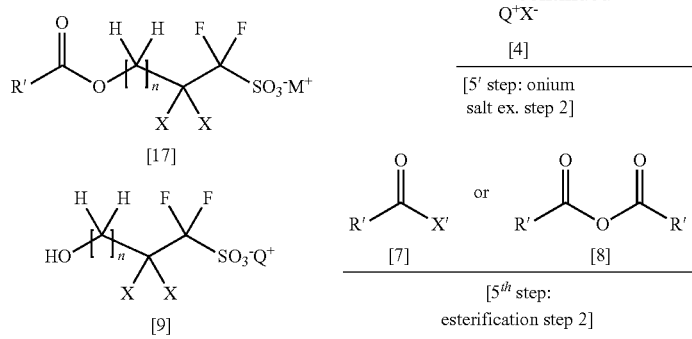

That is, it is a method in which a hydroxyfluoroalkanesulfonic acid salt represented by general formula [6] is esterified to obtain a fluoroalkanesulfonic acid salt represented by general formula [17] (4' step: esterification step 2), and furthermore this is subjected to an onium salt exchange by using a monovalent onium salt represented by general formula [4] to produce a fluoroalkanesulfonic acid onium salt represented by general formula [10] (5' step: onium salt exchange step 2).

In this method, however, there were problems such as the completion of the reaction in the 4' step (esterification step 2) being difficult, and therefore the purification of the target product being difficult, etc.

Therefore, as mentioned above, it is a preferable method to conduct the fourth step and the fifth step of the present invention in this order.

[Previous Step: Ester Exchange Step 1]

Finally, the previous step of the present invention is explained. The previous step is a step in which the corresponding bromofluoroalcohol is reacted with a carboxylic acid derivative represented by general formula [11] or general formula [12] to conduct an esterification, thereby producing a carboxylic acid bromofluoroalkyl ester represented by general formula [1].

In the present step, it is possible to produce a carboxylic acid bromofluoroalkyl ester represented by general formula [1] from the corresponding bromofluoroalcohol by using a method similar to the fifth step, except in that carboxylic acids and carboxylic halides represented by general formula [11] are used in place of carboxylic acids and carboxylic halides represented by general formula [7] in the fifth step, and that carboxylic anhydrides represented by general formula [12] are used in place of carboxylic anhydrides represented by general formula [8].

EXAMPLES

In the following, the present invention is explained in more detail by giving examples, but the present invention is not limited by these.

Example 1-1

Production of 6-bromo-5,5,6,6-tetrafluorohexane benzoate

The Previous Step: Esterification Step 1

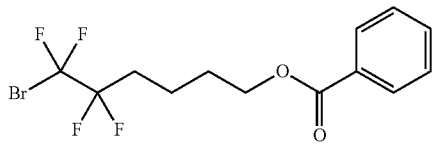 [SMILES: O=C(OCCCCC(F)(F)C(F)(F)Br)c1ccccc1]

A 300 mL reactor was charged under nitrogen with 14.0 g (99.6 mmol/1.3 equivalents) of benzoyl chloride and 150 mL of tetrahydrofuran (a dehydrated product), following by putting it in an ice bath. 20.0 g (79.0 mmol/1.0 equivalent) of 6-bromo-5,5,6,6-tetrafluorohexan-1-ol was added thereto, followed by adding dropwise of 12.0 g (119 mmol/1.5 equivalents) of triethylamine. After the dropping, stirring was conducted at 60 degrees for 10 hours. Then, 100 mL of water was added, and extraction was conducted two times with 200 mL of diisopropyl ether. The obtained organic layer was washed further with diluted hydrochloric acid, sodium bicarbonate water and brine, followed by removing water by sodium sulfate and conducting filtration. Then, isopropyl ether was distilled out, thereby obtaining 24.4 g of the target 6-bromo-5,5,6,6-tetrafluorohexane benzoate. Upon this, purity was 95%, and yield was 82%.

Properties of 6-bromo-5,5,6,6-tetrafluorohexane benzoate $^1$H NMR (measurement solvent: heavy dimethyl sulfoxide, standard substance: tetramethylsilane); $\delta$=7.99 (m, 2H), 7.65 (m, 1H), 7.50 (m, 2H), 4.01 (m, 2H), 2.07 (m, 2H), 1.58 (m, 4H)

$^{19}$F NMR (measurement solvent: heavy dimethyl sulfoxide, standard substance: trichlorofluoromethane), $\delta$=−66.1 (s, 2F), −110.9 (s, 2F)

Example 1-2

Production of triethylammonium 1,1,2,2-tetrafluoro-6-benzoyloxyhexane-1-sulfinato First Step: Sulfinating Step

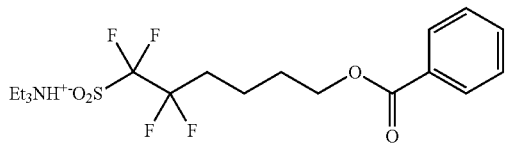

A 200 mL reactor was charged with 20.0 g (purity 95%, 53.2 mmol) of 6-bromo-5,5,6,6-tetrafluorohexane benzoate obtained by Example 1-1, 50 g of acetonitrile, 40 g of water, 15.0 g (86.4 mmol/1.6 equivalents) of sodium dithionite, and 9.8 g (97.2 mmol/1.8 equivalents) of triethylamine in order, followed by stirring at 60° C. for 3 hours. The reaction liquid was separated into an organic layer and an aqueous layer. Acetonitrile was distilled out of the organic layer, followed by adding 40 mL of dichloromethane to prepare a dichloromethane solution. Extraction was conducted on the aqueous layer with 20 mL of dichloromethane, and this was combined with the organic layer. The obtained organic layer was washed with 10% sodium thiosulfate aqueous solution, water and brine, followed by distilling dichloromethane off, thereby obtaining 24.4 g of the target triethylammonium 1,1,2,2-tetrafluoro-6-benzoyloxyhexane-1-sulfinato. Upon this, purity was 85%, and yield was 88%. No devitrification was found in the glass flask used when distilling dichloromethane off.

Properties of triethylammonium 1,1,2,2-tetrafluoro-6-benzoyloxyhexane-1-sulfinato $^1$H NMR (measurement solvent: heavy dimethyl sulfoxide, standard substance: tetramethylsilane); δ=7.85 (m, 2H), 7.20 (m, 2H), 7.46 (m, 1H), 4.01 (m, 2H), 3.10 (m, 6H), 2.17 (m, 2H), 1.61 (m, 4H), 1.18 (t, 9H)

$^{19}$F NMR (measurement solvent: heavy dimethyl sulfoxide, standard substance: trichlorofluoromethane), δ=−111.2 (s, 2F), −130.1 (s, 2F)

Example 1-3

Production of triethylammonium 1,1,2,2-tetrafluoro-6-benzoyloxyhexane-1-sulfinato Second Step: Oxidation Step

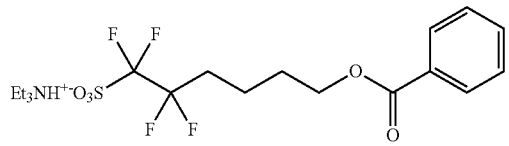

A 200 mL reactor was charged with 20.0 g (purity 85%, 38.3 mmol) of triethylammonium 1,1,2,2-tetrafluoro-6-benzoyloxyhexane-1-sulfinato obtained by Example 1-2, 100 mL of water, 0.019 g (0.057 mmol/0.0015 equivalents) of disodium tungstate dihydrate, and 6.1 g (53.6 mmol/1.4 equivalents) of 30% hydrogen peroxide water, followed by stirring at room temperature for 3 hours. Then, the reaction liquid was ascertained by $^{19}$F NMR that triethylammonium 1,1,2,2-tetrafluoro-6-benzoyloxyhexane-1-sulfinato was completely consumed and that the production of 6-bromo-5,5,6,6-tetrafluorohexane benzoate as a by-product was <1%. Extraction was conducted two times on the reaction liquid with 40 mL of dichloromethane. Out of the obtained organic layer, the solvent was distilled, and the obtained solid matter was dried. The solid matter was dissolved in methanol, and insoluble matters were filtered out to prepare a methanol solution. The obtained methanol solution was added dropwise to isopropyl ether, followed by stirring at room temperature for 1 hour. Then, the precipitated solid matter was filtered and dried, thereby obtaining 14.5 g of the target triethylammonium 1,1,2,2-tetrafluoro-6-benzoyloxyhexane-1-sulfonato. Upon this, purity was 98%, and yield was 81%.

Properties of triethylammonium 1,1,2,2-tetrafluoro-6-benzoyloxyhexane-1-sulfonato $^1$H NMR (measurement solvent: heavy dimethyl sulfoxide, standard substance: tetramethylsilane); δ=7.85 (m, 2H), 7.20 (m, 2H), 7.46 (m, 1H), 4.01 (m, 2H), 3.10 (m, 6H), 2.17 (m, 2H), 1.61 (m, 4H), 1.18 (t, 9H)

$^{19}$F NMR (measurement solvent: heavy dimethyl sulfoxide, standard substance: trichlorofluoromethane), δ=112.0 (s, 2F), −117.3 (s, 2F)

Example 1-4

Production of triphenylsulfonium 1,1,2,2-tetrafluoro-6-benzoyloxyhexane-1-sulfonato Third Step: Onium Salt Exchange Step 1

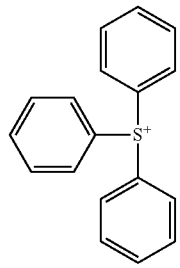

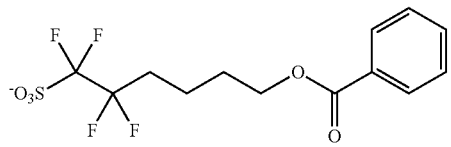

A 500 mL reactor was charged with 14.0 g (purity 98%, 29.9 mmol) of triethylammonium 1,1,2,2-tetrafluoro-6-benzoyloxyhexane-1-sulfonato obtained by Example 1-3 and 150 g of water, followed by adding dropwise a triphenylsulfonium bromide aqueous solution [11.3 g (33.0 mmol/1.1 equivalents) of triphenylsulfonium bromide and 150 g of water] at room temperature. Then, stirring was conducted at room temperature for 2 hours, followed by conducting a filtration and drying the solid matter, thereby obtaining 17.2 g of the target triphenylsulfonium 1,1,2,2-tetrafluoro-6-benzoyloxyhexane-1-sulfonato. Upon this, purity was 98%, and yield was 91%.

Properties of triphenylsulfonium 1,1,2,2-tetrafluoro-6-benzoyloxyhexane-1-sulfonato $^1$H NMR (measurement solvent: heavy dimethyl sulfoxide, standard substance: tetramethylsilane); δ=7.85 (m, 2H), 7.65 (m, 15H), 7.46 (m, 1H), 7.20 (m, 2H), 4.01 (m, 2H), 2.07 (m, 2H), 1.61 (m, 4H) $^{19}$F NMR (measurement solvent: heavy dimethyl sulfoxide, standard substance: trichlorofluoromethane), δ=113.0 (s, 2F), −117.3 (s, 2F)

Example 2-1

Production of 6-bromo-5,5,6,6-tetrafluorohexane cyclohexanecarboxylate

The Previous Step: Esterification Step 1

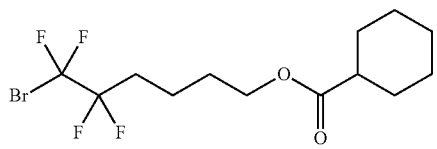 [SMILES: O=C(OCCCCC(F)(F)C(F)(F)Br)C1CCCCC1]

A 300 mL reactor was charged under nitrogen with 14.7 g (100 mmol/1.3 equivalents) of cyclohexanecarbonyl chloride and 150 mL of tetrahydrofuran (a dehydrated product), followed by putting it in an ice bath. 20.0 g (79.0 mmol/1.0 equivalent) of 6-bromo-5,5,6,6-tetrafluorohexan-1-ol was added thereto, followed by adding dropwise of 12.0 g (119 mmol/1.5 equivalents) of triethylamine. After the dropping, stirring was conducted at 60 degrees for 6 hours. Then, 100 mL of water was added, and extraction was conducted two times with 200 mL of diisopropyl ether. The obtained organic layer was washed further with diluted hydrochloric acid, sodium bicarbonate water and brine, followed by removing water by sodium sulfate and conducting filtration. Then, isopropyl ether was distilled out, thereby obtaining 27.5 g of the target 6-bromo-5,5,6,6-tetrafluorohexane cyclohexanecarboxylate. Upon this, purity was 94%, and yield was 90%.

Properties of 6-bromo-5,5,6,6-tetrafluorohexane cyclohexanecarboxylate $^1$H NMR (measurement solvent: heavy dimethyl sulfoxide, standard substance: tetramethylsilane); δ=4.01 (m, 2H), 2.25 (m, 1H), 2.07 (m, 2H), 1.80 (m, 4H), 1.58 (m, 4H), 1.42 (m, 6H)

$^{19}$F NMR (measurement solvent: heavy dimethyl sulfoxide, standard substance: trichlorofluoromethane), δ=−66.1 (s, 2F), −110.9 (s, 2F)

Example 2-2

Production of triethylammonium 1,1,2,2-tetrafluoro-6-cyclohexylcarbonyloxyhexane-1-sulfinato First Step: Sulfinating Step

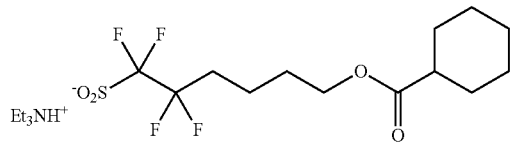

A 200 mL reactor was charged with 20.0 g (purity 94%, 51.8 mmol) of 6-bromo-5,5,6,6-tetrafluorohexane cyclohexanecarboxylate obtained by Example 2-1, 50 g of acetonitrile, 40 g of water, 15.0 g (86.4 mmol/1.7 equivalents) of sodium dithionite, and 10.0 g (99.2 mmol/1.9 equivalents) of triethylamine in order, followed by stirring at 60° C. for 3 hours. The reaction liquid was separated into an organic layer and an aqueous layer. Acetonitrile was distilled out of the organic layer, followed by adding 40 mL of dichloromethane to prepare a dichloromethane solution. Extraction was conducted on the aqueous layer with 20 mL of dichloromethane, and this was combined with the organic layer. The obtained organic layer was washed with 10% sodium thiosulfate aqueous solution, water and brine, followed by distilling dichloromethane off, thereby obtaining 25.3 g of the target triethylammonium 1,1,2,2-tetrafluoro-6-cyclohexylcarbonyloxyhexane-1-sulfinato. Upon this, purity was 83%, and yield was 90%. No devitrification was found in the glass flask used when distilling dichloromethane off.

Properties of triethylammonium 1,1,2,2-tetrafluoro-6-cyclohexylcarbonyloxyhexane-1-sulfinato $^1$H NMR (measurement solvent: heavy dimethyl sulfoxide, standard substance: tetramethylsilane); δ=4.01 (m, 2H), 3.10 (m, 6H), 2.26 (m, 1H), 2.17 (m, 2H), 1.54 (m, 4H), 1.23 (m, 6H), 1.61 (m, 4H), 1.18 (t, 9H)

$^{19}$F NMR (measurement solvent: heavy dimethyl sulfoxide, standard substance: trichlorofluoromethane), δ=−111.2 (s, 2F), −130.1 (s, 2F)

Example 2-3

Production of triethylammonium 1,1,2,2-tetrafluoro-6-cyclohexylcarbonyloxyhexane-1-sulfonato Second Step: Oxidation Step

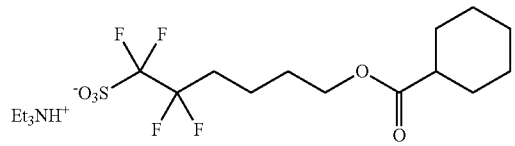

A 200 mL reactor was charged with 20.0 g (purity 83%, 36.9 mmol) of triethylammonium 1,1,2,2-tetrafluoro-6-cyclohexylcarbonyloxyhexane-1-sulfinato obtained by Example 2-2, 100 mL of water, 0.018 g (0.055 mmol/0.0015 equivalents) of disodium tungstate dihydrate, and 6.0 g (52.7 mmol/1.4 equivalents) of 30% hydrogen peroxide water, followed by stirring at room temperature for 3 hours. Then, the reaction liquid was ascertained by $^{19}$F NMR that triethylammonium 1,1,2,2-tetrafluoro-6-cyclohexylcarbonyloxyhexane-1-sulfinato was completely consumed and that the production of 6-bromo-5,5,6,6-tetrafluorohexane cyclohexanecarboxylate as a by product was <1%. Extraction was conducted two times on the reaction liquid with 40 mL of dichloromethane. Out of the obtained organic layer, the solvent was distilled, and the obtained solid matter was dried. The solid matter was dissolved in methanol, and insoluble matters were filtered out to prepare a methanol solution. The obtained methanol solution was added dropwise to isopropyl ether, followed by stirring at room temperature for 1 hour. Then, the precipitated solid matter was filtered and dried, thereby obtaining 14.9 g of the target triethylammonium 1,1,2,2-tetrafluoro-6-cyclohexylcarbonyloxyhexane-1-sulfonato. Upon this, purity was 98%, and yield was 85%.

Properties of triethylammonium 1,1,2,2-tetrafluoro-6-cyclohexylcarbonyloxyhexane-1-sulfonato $^1$H NMR (measurement solvent: heavy dimethyl sulfoxide, standard substance: tetramethylsilane); δ=4.01 (m, 2H), 3.10 (m, 6H), 2.26 (m, 1H), 2.17 (m, 2H), 1.54 (m, 4H), 1.23 (m, 6H), 1.61 (m, 4H), 1.18 (t, 9H)

$^{19}$F NMR (measurement solvent: heavy dimethyl sulfoxide, standard substance: trichlorofluoromethane), δ=−112.0 (s, 2F), −117.3 (s, 2F)

Example 2-4

Production of triphenylsulfonium 1,1,2,2-tetrafluoro-6-cyclohexylcarbonyloxyhexane-1-sulfonato Third Step: Onium Salt Exchange Step 1

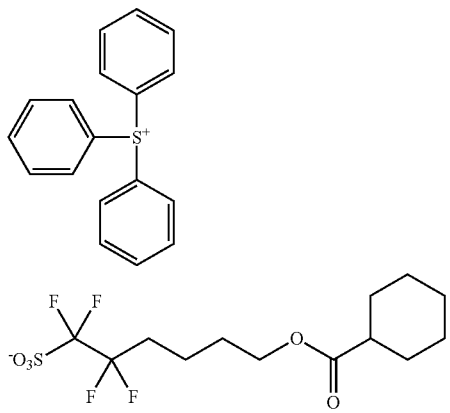

A 500 mL reactor was charged with 14.0 g (purity 98%, 29.5 mmol) of triethylammonium 1,1,2,2-tetrafluoro-6-cyclohexylcarbonyloxyhexane-1-sulfonato obtained by Example 2-3 and 150 g of water, followed by adding dropwise a triphenylsulfonium bromide aqueous solution [11.0 g (32.1 mmol/1.1 equivalents) of triphenylsulfonium bromide and 150 g of water] at room temperature. Then, stirring was conducted at room temperature for 2 hours, followed by conducting a filtration and drying the solid matter, thereby obtaining 16.8 g of the target triphenylsulfonium 1,1,2,2-tetrafluoro-6-cyclohexylcarbonyloxyhexane-1-sulfonato. Upon this, purity was 98%, and yield was 89%.

Properties of triphenylsulfonium 1,1,2,2-tetrafluoro-6-cyclohexylcarbonyloxyhexane-1-sulfonato $^1$H NMR (measurement solvent: heavy dimethyl sulfoxide, standard substance: tetramethylsilane); δ=7.65 (m, 15H), 4.01 (m, 2H), 2.26 (m, 1H), 2.07 (m, 2H), 1.54 (m, 4H), 1.23 (m, 6H), 1.58 (m, 4H)

$^{19}$F NMR (measurement solvent: heavy dimethyl sulfoxide, standard substance: trichlorofluoromethane), δ=−113.0 (s, 2F), −117.3 (s, 2F)

Example 3-1

Production of sodium 1,1,2,2-tetrafluoro-6-hydroxyhexanesulfonate

3' Step: Saponification Step

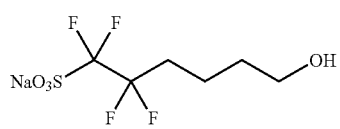

A 2 L reactor was charged with 20.0 g (purity 98%, 42.7 mmol) of triethylammonium 1,1,2,2-tetrafluoro-6-benzoyloxyhexane-1-sulfonato obtained by the same method as that of Example 1-3, 50 mL of water, and 10 g (120 mmol/2.8 equivalents) of 48% sodium hydroxide aqueous solution, followed by stirring at room temperature for 2 hours. Then, 15 g (152 mmol/3.6 equivalents) of 37% hydrochloric acid aqueous solution was added, followed by stirring at room temperature for 1 hour and washing two times with 30 mL of diisopropyl ether. The solvent was distilled out of the obtained aqueous layer, thereby obtaining 14.9 g of the target sodium 1,1,2,2-tetrafluoro-6-hydroxyhexanesulfonate. Upon this, purity was 75%, and yield was 95%.

Properties of sodium 1,1,2,2-tetrafluoro-6-hydroxyhexanesulfonate $^1$H NMR (measurement solvent: heavy dimethyl sulfoxide, standard substance: tetramethylsilane); δ=6.40 (s, 1H), 5.85 (m, 1H), 4.46 (t, 2H), 2.77 (m, 2H), 2.27 (m, 4H), 2.23 (s, 3H)

$^{19}$F NMR (measurement solvent: heavy dimethyl sulfoxide, standard substance: trichlorofluoromethane), δ=−112.5 (s, 2F), −118.1 (s, 2F)

Example 3-2

Production of triphenylsulfonium 1,1,2,2-tetrafluoro-6-hydroxyhexanesulfonato

Fourth Step: Onium Salt Exchange Step 2

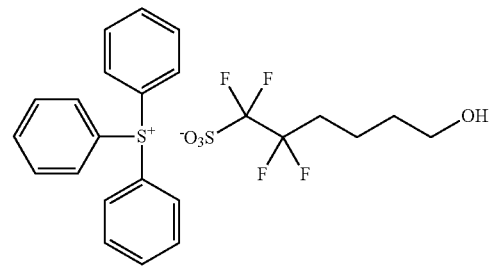

A 500 mL reactor was charged with 14.0 g (purity 75%, 38.0 mmol) of sodium 1,1,2,2-tetrafluoro-6-hydroxyhexanesulfonate obtained by Example 3-1 and 150 g of water, followed by adding dropwise a triphenylsulfonium bromide aqueous solution [14.3 g (41.8 mmol/1.1 equivalents) of triphenylsulfonium bromide and 150 g of water] at room temperature. Then, stirring was conducted at room temperature for 2 hours, followed by conducting a filtration and drying the solid matter, thereby obtaining 18.0 g of the target triphenylsulfonium 1,1,2,2-tetrafluoro-6-hydroxyhexanesulfonato. Upon this, purity was 98%, and yield was 90%.

Properties of triphenylsulfonium 1,1,2,2-tetrafluoro-6-hydroxyhexanesulfonato $^1$H NMR (measurement solvent: heavy dimethyl sulfoxide, standard substance: tetramethylsilane); δ=7.90 (m, 15H), 4.43 (s, 1H), 3.37 (m, 2H), 2.15 (m, 2H), 1.47 (m, 4H)

$^{19}$F NMR (measurement solvent: heavy dimethyl sulfoxide, standard substance: trichlorofluoromethane), δ=−111.9 (s, 2F), −117.3 (s, 2F)

Example 3-3

Production of triphenylsulfonium 1,1,2,2-tetrafluoro-6-methacryloyloxyhexanesulfonato Fifth Step: Esterification Step 2

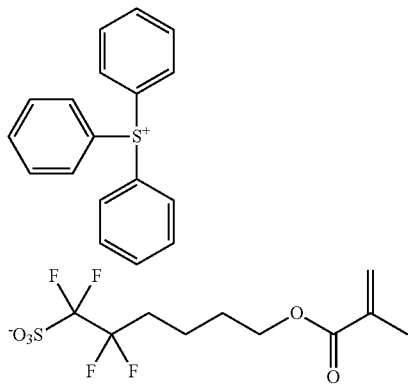

A 300 mL reactor was charged with 15.0 g (purity 98%, 35.1 mmol) of triphenylsulfonium 1,1,2,2-tetrafluoro-6-hydroxyhexanesulfonato obtained by Example 3-2, 75 ml of acetonitrile, 1 mg of NONFLEX MBP, and 10.7 g (70 mmol/2.0 equivalents) of methacrylic anhydride in order, followed by putting it in an ice bath. 10.7 g (105 mmol/3.0 equivalents) of triethylamine was added dropwise thereto. After the dropping, stirring was conducted at room temperature for 6 hours. Then, 50 mL of water was added, and acetonitrile was distilled out. The obtained aqueous layer was washed two times with 20 mL of isopropyl ether, thereby obtaining 19.3 g of the target triphenylsulfonium 1,1,2,2-tetrafluoro-6-methacryloyloxyhexanesulfonato. Upon this, purity was 98%, and yield was 92%.

Properties of triphenylsulfonium 1,1,2,2-tetrafluoro-6-methacryloyloxyhexanesulfonato $^1$H NMR (measurement solvent: heavy dimethyl sulfoxide, standard substance: tetramethylsilane); δ=8.06 (m, 15H), 6.40 (s, 1H), 5.85 (m, 1H), 4.46 (t, 2H), 2.77 (m, 2H), 2.27 (m, 4H), 2.23 (s, 3H)
$^{19}$F NMR (measurement solvent: heavy dimethyl sulfoxide, standard substance: trichlorofluoromethane), δ=−113.5 (s, 2F), −118.1 (s, 2F)

Comparative Example 1-1

Production of sodium 1,1,2,2-tetrafluoro-6-benzoyloxyhexane-1-sulfinate

First Step: Sulfinating Step

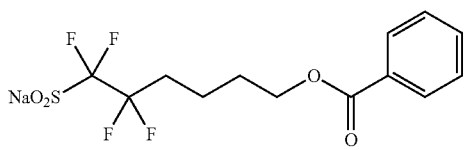

A 100 mL reactor was charge with 10.0 g (purity 95%, 26.6 mmol) of 6-bromo-5,5,6,6-tetrafluorohexane benzoate obtained by the same method as that of Example 1-1, 25 g of acetonitrile, 20 g of water, 7.5 g (43.2 mmol/1.6 equivalents) of sodium dithionite, and 4.0 g (47.6 mmol/1.8 equivalents) of sodium hydrogencarbonate in order, followed by stirring at 60° C. for 48 hours. The 6-bromo-5,5,6,6-tetrafluorohexane benzoate was, however, not completely consumed, and conversion was 80%. Furthermore, 7.5 g (43.2 mmol/1.6 equivalents) of sodium dithionite and 4.0 g (47.6 mmol/1.8 equivalents) of sodium hydrogencarbonate were added, followed by stirring at 60° C. for 24 hours. With this, conversion was improved to 90%, but the raw material was still not consumed completely.

In the reaction liquid separated into two layers, the fluorine ion concentration of the aqueous layer was 240 ppm. As the organic layer was put into a glass flask and concentration was conducted, the glass flask was devitrified. The solid matter resulting from concentrating the organic layer was washed with 100 mL of diisopropyl ether, followed by conducting a filtration and drying the solid matter, thereby obtaining 10.3 g of the target sodium 1,1,2,2-tetrafluoro-6-benzoyloxyhexane-1-sulfinate. Upon this, yield was 51%, and purity was 48%.

Thus, in the case of using sodium hydrogencarbonate as the base, the reaction time is long, and furthermore the reaction is not completed. Furthermore, yield is also low, and purity of the target product to be obtained is also low.

Furthermore, the glass instrument is corroded by the effect of fluorine ions to be released.

Comparative Example 1-2

Production of sodium 1,1,2,2-tetrafluoro-6-cyclohexylcarbonyloxyhexane-1-sulfinate First Step: Sulfinating Step

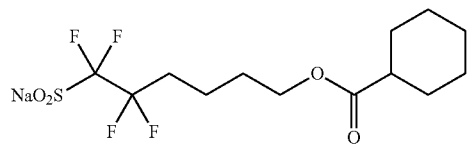

A 100 mL reactor was charged with 10.0 g (purity 95%, 26.2 mmol) of 6-bromo-5,5,6,6-tetrafluorohexane cyclohexanecarboxylate obtained by the same method as that of Example 2-1, 25 g of acetonitrile, 20 g of water, 7.5 g (43.2 mmol/1.6 equivalents) of sodium dithionite, and 4.0 g (47.6 mmol/1.8 equivalents) of sodium hydrogencarbonate in order, followed by stirring at 60° C. for 48 hours. The 6-bromo-5,5,6,6-tetrafluorohexane cyclohexanecarboxylate was, however, not consumed completely, and conversion was 66%. Of the reaction liquid separated into two layers, the aqueous layer was discarded. Furthermore, 20 g of water, 7.5 g (43.2 mmol/1.6 equivalents) of sodium dithionite and 4.0 g (47.6 mmol/1.8 equivalents) of sodium hydrogencarbonate were added, followed by stirring at 60° C. for 24 hours. With this, conversion was improved to 87%. Again, the aqueous layer was discarded. Furthermore, 20 g of water, 7.5 g (43.2 mmol/1.6 equivalents) of sodium dithionite and 4.0 g (47.6 mmol/1.8 equivalents) of sodium hydrogencarbonate were added, followed by stirring at 60° C. for 24 hours. With this, the raw material disappeared completely.

The reaction liquid was extracted one time with 30 mL of acetonitrile. The obtained organic layer was concentrated, and the solvent was distilled out. The solid matter obtained after the concentration was washed with 100 mL of diisopropyl ether, followed by conducting filtration and drying the solid matter, thereby obtaining 11.2 g of the target sodium 1,1,2,2-tetrafluoro-6-cyclohexylcarbonyloxyhexane-1-sulfinate. Upon this, yield was 45%, and purity was 39%.

In this manner, it is necessary in the middle of the reaction to discard the aqueous layer and add sodium dithionite and sodium hydrogencarbonate.

Comparative Example 2-1

Production of sodium 1,1,2,2-tetrafluoro-6-cyclohexylcarbonyloxyhexane-1-sulfonate Second Step: Oxidation Step

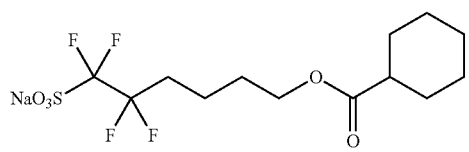

A glass flask equipped with a thermometer, a condenser and a dropping funnel was charged with 10.0 g (10.5 mmol) of sodium 1,1,2,2-tetrafluoro-6-cyclohexylcarbonyloxyhexane-1-sulfinate having a purity of 39% obtained by Comparative Example 1-2, a catalytic amount of sodium tungstate dihydrate, and 10 ml of water, followed by stirring. Then, 2.4 g (21.0 mmol) of 30% hydrogen peroxide water was added dropwise in an ice bath. After terminating the dropping, stirring was continued at room temperature for one hour. The reaction termination was confirmed by $^{19}$F NMR. After concentrating the reaction liquid, it was washed with 10 ml of diisopropyl ether, followed by filtration and drying the obtained solid matter. After that, there was obtained as a white-color solid matter 9.1 g (yield 90%, purity 40%) of sodium 1,1,2,2-tetrafluoro-6-cyclohexylcarbonyloxyhexane-1-sulfonate. Upon this, 7% of 6-bromo-5,5,6,6-tetrafluorohexane cyclohexanecarboxylate was produced as a by-product.

Comparative Example 2-2

Production of triethylammonium 1,1,2,2-tetrafluoro-6-benzoyloxyhexane-1-sulfonato Second Step: Oxidation Step

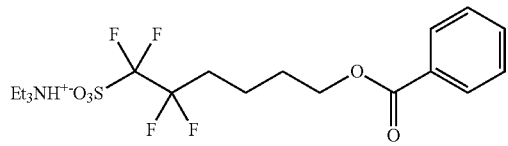

A 200 mL reactor was charged with 20.0 g (purity 95%, 53.2 mmol) of 6-bromo-5,5,6,6-tetrafluorohexane benzoate obtained by the same method as that of Example 1-1, 50 g of acetonitrile, 40 g of water, 15.0 g (86.4 mmol/1.6 equivalents) of sodium dithionite, and 9.8 g (97.2 mmol/1.8 equivalents) of triethylamine in order, followed by stirring at 60° C. for 3 hours. The reaction liquid was separated (without conducting a washing by water and a washing by a sodium thiosulfate aqueous solution or a sodium sulfite aqueous solution), and the solvent was distilled out of the organic layer, thereby obtaining 33.4 g of the target triethylammonium 1,1,2,2-tetrafluoro-6-benzoyloxyhexane-1-sulfinato. Upon this, purity was 60%, and yield was 85%.

33.4 g (purity 60%, 45.2 mmol) of the obtained triethylammonium 1,1,2,2-tetrafluoro-6-benzoyloxyhexane-1-sulfinato, 100 mL of water, 0.021 g (0.066 mmol/0.0015 equivalents) of disodium tungstate dihydrate, and 7.0 g (61.2 mmol/1.4 equivalents) of 30% hydrogen peroxide water were added, followed by stirring at room temperature for 3 hours. Then, the reaction liquid was checked by $^{19}$F NMR. With this, triethylammonium 1,1,2,2-tetrafluoro-6-benzoyloxyhexane-1-sulfinato was consumed completely, and the production of 6-bromo-5,5,6,6-tetrafluorohexane benzoate as a by-product was 12%. The reaction liquid was extracted two times with 40 mL of dichloromethane. Dichloromethane of the obtained organic layer was distilled out, and the obtained solid matter was dried. The solid matter was dissolved in methanol, and insoluble matters were filtered out to prepare a methanol solution. The obtained methanol solution was added dropwise to isopropyl ether, followed by stirring at room temperature for 1 hour. Then, the precipitated solid matter was separated by filtration and dried, thereby obtaining 12.7 g of the target triethylammonium 1,1,2,2-tetrafluoro-6-benzoyloxyhexane-1-sulfinato. Upon this, purity was 98%, and yield was 60%.

Thus, when the solvent is distilled out of the organic layer without conducting a washing by water and a washing by a sodium thiosulfate aqueous solution or a sodium sulfite aqueous solution in the sulfinating step, 6-bromo-5,5,6,6-tetrafluorohexane benzoate is produced as a by-product in the oxidation step of the next step.

Comparative Example 3

Production of triethylammonium 1,1,2,2-tetrafluoro-6-methacryloyloxyhexanesulfinato First Step: Sulfinating Step

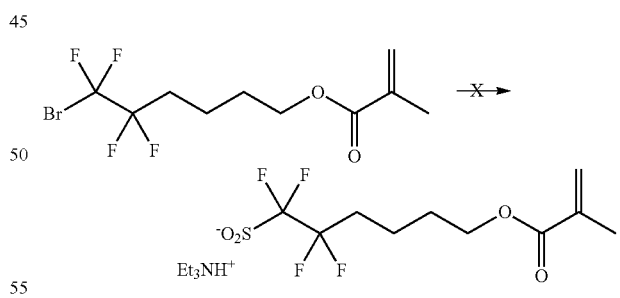

A 300 mL reactor was charged under nitrogen with 18.2 g (119 mmol/1.5 equivalents) of methacrylic anhydride and 150 mL of acetonitrile, followed by putting it in an ice bath. 20.0 g (79.0 mmol/1.0 equivalent) of 6-bromo-5,5,6,6-tetrafluorohexan-1-ol was added thereto, followed by adding dropwise of 12.0 g (119 mmol/1.5 equivalents) of triethylamine. After the dropping, stirring was conducted at 60 degrees for 10 hours. Then, 100 mL of water was added, and extraction was conducted two times with 200 mL of diisopropyl ether. The obtained organic layer was washed further with diluted hydrochloric acid, sodium bicarbonate water and brine, followed by removing water by sodium sulfate and conducting filtration. Then, isopropyl ether was distilled out, thereby obtaining 23.8 g of the target 6-bromo-5,5,6,6-tetrafluorohexane methacrylate. Upon this, purity was 96%, and yield was 90%.

It was charged with 20 g (purity 96%, 16.7 mmol/1.0 equivalent) of the obtained 6-bromo-5,5,6,6-tetrafluorohexane methacrylate, 40 g of acetonitrile and 40 g of water. Then, stirring was started, and then 3.0 g (30 mmol/1.8 equivalents) of triethylamine and 5.0 g (28.4 mmol/1.7 equivalents) of sodium dithionite were added. Then, stirring was conducted at 60° C. for 2 hours. The organic layer of the reaction liquid was analyzed by using a nuclear magnetic resonator (NMR). With this, the target triethylammonium 1,1,2,2-tetrafluoro-6-methacryloyloxyhexanesulfinato was not detected, but there was detected only a by-product in which only the methacrylic moiety was decomposed.

Comparative Example 4

Production of sodium 1,1,2,2-tetrafluoro-6-methacryloyloxyhexanesulfonate

4' Step: Esterification Step 2

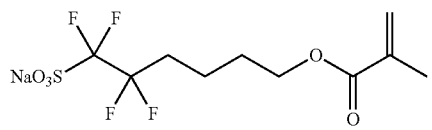

A 300 mL reactor was charged with 11.0 g (purity 75%, 30 mmol) of sodium 1,1,2,2-tetrafluoro-6-hydroxyhexanesulfonate, 75 ml of acetonitrile, 1 mg of NONFLEX MBP, and 9.2 g (60 mmol/2.0 equivalents) of methacrylic anhydride in order, followed by putting it into an ice bath. 9.2 g (90 mmol/3.0 equivalents) of triethylamine was added thereto dropwise. After the dropping, stirring was conducted at room temperature for 6 hours. The organic layer of the reaction liquid was analyzed by using a nuclear magnetic resonator (NMR). With this, conversion was 55%. Then, furthermore 9.2 g (60 mmol/2.0 equivalents) of methacrylic anhydride was added. The temperature was raised to 40° C., and the reaction was conducted for 12 hours. Conversion was, however, stopped at 80%. Then, 40 mL of water was added, and acetonitrile was distilled out. The obtained aqueous layer was washed two times with 15 mL of isopropyl ether to try to obtain the target sodium 1,1,2,2-tetrafluoro-6-methacryloyloxyhexanesulfonate. It was, however, difficult to conduct a separation from the raw material sodium 1,1,2,2-tetrafluoro-6-hydroxyhexanesulfonate.

The obtained mixture of sodium 1,1,2,2-tetrafluoro-6-methacryloyloxyhexanesulfonate and sodium 1,1,2,2-tetrafluoro-6-hydroxyhexanesulfonate and 150 g of water were added, and a triphenylsulfonium bromide aqueous solution [20.0 g (58.4 mmol) of triphenylsulfonium bromide and 300 g of water] was added dropwise at room temperature. Then, stirring was conducted at room temperature for 2 hours, followed by conducting a filtration. After adding 1 mg of NONFLEX MBP, the solid matter was dried, thereby obtaining 15.1 g of the target triphenylsulfonium 1,1,2,2-tetrafluoro-6-methacryloyloxyhexanesulfonato. Purity was, however, 76%, and 22% of triphenylsulfonium 1,1,2,2-tetrafluoro-6-hydroxyhexanesulfonato was contained.

The invention claimed is:
1. A fluoroalkanesulfinic acid ammonium salt represented by the following general formula [2]

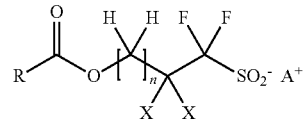

wherein $A^+$ represents an ammonium ion, and
R represents (a) a $C_{1-10}$ straight-chain or branched alkyl group, (b) a $C_{3-20}$ alicyclic organic group, (c) an organic group formed of a $C_{3-20}$ alicyclic organic group and a straight-chain alkylene group, (d) a $C_{3-30}$ monocyclic or polycyclic lactone, or (e) $C_{6-20}$ aryl group,
hydrogen atoms on the alkyl group, the alicyclic organic group, the organic group formed of the alicyclic organic group and the straight-chain alkylene group, the monocyclic or polycyclic lactone, and the aryl group may partially or completely be replaced with fluorine, hydroxyl group, hydroxycarbonyl group, or a $C_{1-6}$ straight-chain, branched or cyclic alkoxy group,
two hydrogen atoms on the same carbon forming the alkyl group, the alicyclic organic group or the organic group formed of the alicyclic organic group and the straight-chain alkylene group may be replaced with one oxygen atom to become a keto group,
one having a nonconjugated unsaturated moiety (a double bond or triple bond) in the structure is excluded as R,
each X independently represents a group selected from the group consisting of hydrogen atom, fluorine atom, a $C_{1-6}$ alkyl group, and a $C_{1-6}$ fluorine-containing alkyl group,
n represents an integer of 1-8.
2. A salt according to claim 1, wherein $A^+$ is an ammonium ion represented by general formula [I]

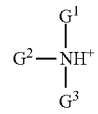

wherein $G^1$, $G^2$ and $G^3$ mutually independently represent hydrogen atoms, $C_{1-6}$ alkyl groups, $C_{1-6}$ alkoxyalkyl groups, $C_{3-12}$ cycloalkyl groups, optionally substituted phenyl groups, optionally substituted $C_{7-12}$ aralkyl groups, optionally substituted naphthyl groups, optionally substituted $C_{5-10}$ hetero aromatic groups, or a ring optionally containing a hetero atom by at least two of $G^1$, $G^2$ and $G^3$.
3. A method for producing a fluoroalkanesulfinic acid ammonium salt represented by general formula [2]

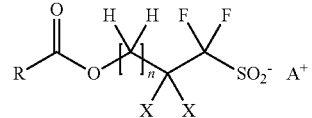

comprising reacting a carboxylic acid bromofluoroalkyl ester represented by the following general formula [1]

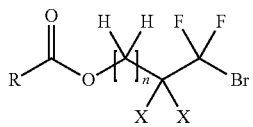

[1]

with a sulfinating agent in the presence of an amine, wherein, R represents (a) a $C_{1-10}$ straight-chain or branched alkyl group, (b) a $C_{3-20}$ alicyclic organic group, (c) an organic group formed of a $C_{3-20}$ alicyclic organic group and a straight-chain alkylene group, (d) a $C_{3-30}$ monocyclic or polycyclic lactone, or (e) $C_{6-20}$ aryl group, hydrogen atoms on the alkyl group, the alicyclic organic group, the organic group formed of the alicyclic organic group and the straight-chain alkylene group, the monocyclic or polycyclic lactone, and the aryl group may partially or completely be replaced with fluorine, hydroxyl group, hydroxycarbonyl group, or a $C_{1-6}$ straight-chain, branched or cyclic alkoxy group, two hydrogen atoms on the same carbon forming the alkyl group, the alicyclic organic group or the organic group formed of the alicyclic organic group and the straight-chain alkylene group may be replaced with one oxygen atom to become a keto group, one having a nonconjugated unsaturated moiety (a double bond or triple bond) in the structure is excluded as R, $A^+$ represents an ammonium ion, each X independently represents a group selected from the group consisting of hydrogen atom, fluorine atom, a $C_{1-6}$ alkyl group, and a $C_{1-6}$ fluorine-containing alkyl group, n represents an integer of 1-8.

4. A method for producing a fluoroalkanesulfonic acid ammonium salt represented by general formula [3]

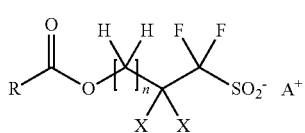

[3]

comprising the following two steps:

a first step (sulfinating step) of obtaining a fluoroalkanesulfinic acid ammonium salt represented by general formula [2]

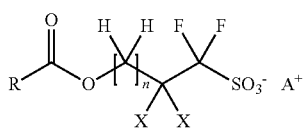

[2]

by reacting a carboxylic acid bromofluoroalkyl ester represented by the following general formula [1]

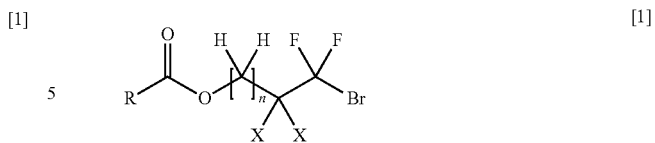

[1]

with a sulfinating agent in the presence of an amine; and a second step (oxidation step) of obtaining a fluoroalkanesulfonic acid ammonium salt represented by general formula [3] by reacting the fluoroalkanesulfinic acid ammonium salt represented by general formula [2] and obtained by the first step (sulfinating step), with an oxidizing agent, wherein in the above general formula [1] to general formula [3], R represents (a) a $C_{1-10}$ straight-chain or branched alkyl group, (b) a $C_{3-20}$ alicyclic organic group, (c) an organic group formed of a $C_{3-20}$ alicyclic organic group and a straight-chain alkylene group, (d) a $C_{3-30}$ monocyclic or polycyclic lactone, or (e) $C_{6-20}$ aryl group, hydrogen atoms on the alkyl group, the alicyclic organic group, the organic group formed of the alicyclic organic group and the straight-chain alkylene group, the monocyclic or polycyclic lactone, and the aryl group may partially or completely be replaced with fluorine, hydroxyl group, hydroxycarbonyl group, or a $C_{1-6}$ straight-chain, branched or cyclic alkoxy group, two hydrogen atoms on the same carbon forming the alkyl group, the alicyclic organic group or the organic group formed of the alicyclic organic group and the straight-chain alkylene group may be replaced with one oxygen atom to become a keto group, one having a nonconjugated unsaturated moiety (a double bond or triple bond) in the structure is excluded as R, $A^+$ represents an ammonium ion, each X independently represents a group selected from the group consisting of hydrogen atom, fluorine atom, a $C_{1-6}$ alkyl group, and a $C_{1-6}$ fluorine-containing alkyl group, n represents an integer of 1-8.

5. A method for producing a fluoroalkanesulfonic acid onium salt represented by general formula [5]

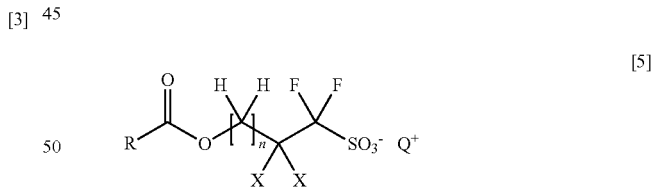

[5]

comprising reacting the fluoroalkanesulfonic acid ammonium salt represented by general formula [3] and obtained by the method of claim 4, with a monovalent onium salt represented by general formula [4]

$Q^+X^-$  [4]

wherein in the above general formula [4], $X^-$ represents a monovalent anion, wherein in the above general formula [5], R has the same meaning as that of R in general formula [1] to general formula [3], wherein in the above general formula [4] and general formula [5], $Q^+$ represents a sulfonium cation represented by the following general formula (a) or the following general formula (b), or an iodonium cation represented by the following general formula (c)

(a)
$$R^1\underset{|}{\overset{+}{\underset{R^3}{S}}}R^2$$

wherein in the above general formula (a), $R^1$, $R^2$ and $R^3$ mutually independently represent substituted or unsubstituted $C_{1-10}$ straight-chain or branched alkyl groups, alkenyl groups or oxoalkyl groups; or substituted or unsubstituted $C_{6-18}$ aryl groups, aralkyl groups or aryloxyalkyl groups; or any two or more of $R^1$, $R^2$ and $R^3$ may be connected with each other to form a ring together with the sulfur atom in the formula (a), (b)
$$(R^4\!-\!\!(O)_n)_m\!\!-\!\!\!\!\bigcirc\!\!-\!\!S^+\!\!-\!\!(\bigcirc)_2$$

wherein in the above general formula (b), $R^4$ represents a substituted or unsubstituted $C_{1-20}$ straight-chain, branched or cyclic alkyl group or alkenyl group; or substituted or unsubstituted $C_{6-14}$ aryl group, m represents an integer of 1-5, and n represents 0 (zero) or 1

(c)
$$((R^4\!-\!\!(O)_n)_q\!\!-\!\!\!\!\bigcirc)_2\!\!-\!\!I^+$$

wherein in the above general formula (c), $R^4$ represents a substituted or unsubstituted $C_{1-20}$ straight-chain, branched or cyclic alkyl group or alkenyl group; or substituted or unsubstituted $C_{6-14}$ aryl group q represents an integer of 0 (zero) to 5, and n represents 0 (zero) or 1.

6. A method for producing a fluoroalkanesulfonic acid onium salt represented by general formula [10]

[10]
$$R\underset{}{\overset{O}{\|}}\!\!-\!\!O\!\!-\!\!\underset{X}{\overset{H}{\underset{|}{C}}}\!\!-\!\!\underset{n}{(\;)}\!\!-\!\!\underset{X}{\overset{F}{\underset{|}{C}}}\!\!-\!\!SO_3^-\;Q^+$$

comprising the steps of:
(a) subjecting a fluoroalkanesulfonic acid ammonium salt represented by general formula [3] and obtained by the method of claim 4 to a saponification to obtain a hydroxyfluoroalkanesulfonic acid salt represented by general formula [6]

[6]
$$HO\!\!-\!\!\underset{X}{\overset{H}{\underset{|}{C}}}\!\!-\!\!\underset{n}{(\;)}\!\!-\!\!\underset{X}{\overset{F}{\underset{|}{C}}}\!\!-\!\!SO_3^-\;M^+$$

(b) reacting the hydroxyfluoroalkanesulfonic acid salt with a monovalent onium salt represented by general formula [4]

$$Q^+X^-$$ [4]

to obtain a hydroxyfluoroalkanesulfonic acid onium salt represented by general formula [9]

[9]
$$HO\!\!-\!\!\underset{X}{\overset{H}{\underset{|}{C}}}\!\!-\!\!\underset{n}{(\;)}\!\!-\!\!\underset{X}{\overset{F}{\underset{|}{C}}}\!\!-\!\!SO_3^-\;Q^+$$

and
(c) reacting the hydroxyfluoroalkanesulfonic acid onium salt with a carboxylic acid derivative represented by general formula [7]

[7]
$$R'\!\!-\!\!\overset{O}{\underset{}{\|}}\!\!-\!\!X'$$

or general formula [8],

[8]
$$R'\!\!-\!\!\overset{O}{\underset{}{\|}}\!\!-\!\!O\!\!-\!\!\overset{O}{\underset{}{\|}}\!\!-\!\!R'$$

wherein in the above general formula [6] and general formula [9], $M^+$ represents a counter cation,
wherein in the above general formula [7], X' represents a hydroxyl group or halogen,
wherein in the above general formula [7] to general formula [10], R' represents (a) a $C_{1-10}$ straight-chain or branched alkyl group, (b) a $C_{1-10}$ straight-chain or branched alkenyl group having a polymerizable double bond at an end portion at least, (c) a $C_{3-20}$ alicyclic organic group, (d) an organic group formed of a $C_{3-20}$ alicyclic organic group and a straight-chain alkylene group, (e) a $C_{3-30}$ monocyclic or polycyclic lactone, or (f) a $C_{6-20}$ aryl group,
hydrogen atoms on the alkyl group, the alkenyl group, the alicyclic organic group, the organic group formed of the alicyclic organic group and the straight-chain alkylene group, the monocyclic or polycyclic lactone, and the aryl group may partially or entirely be replaced with fluorine, hydroxyl group, hydroxycarbonyl group, or $C_{1-6}$ straight-chain, branched or cyclic alkoxy group,
two hydrogen atoms on the same carbon constituting the alkyl group, the alkenyl group, the alicyclic organic group, or the organic group formed of the alicyclic organic group and the straight-chain alkylene group may be replaced with a single oxygen atom to make a keto group, one of the hydrogen atoms on the alkyl group may be replaced with 2-acryloyloxy group or 2-methacryloyloxy group, wherein in the above general formula [10], $Q^+$ has the same meaning as that of $Q^+$ in general formula [4] and general formula [5], each X independently represents a group selected from the group consisting of hydrogen atom, fluorine atom, a $C_{1-6}$ alkyl group, and $C_{1-6}$ fluorine-containing alkyl group, n represents an integer of 1-8.

7. A method according to claim 3, wherein the carboxylic acid bromofluoroalkyl ester is one obtained by an esterification of a bromofluoro alcohol represented by the following general formula [A]

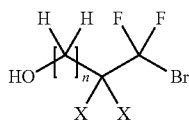

[A]

wherein each X independently represents a group selected from the group consisting of hydrogen atom, fluorine atom, a $C_{1-6}$ alkyl group, and $C_{1-6}$ fluorine-containing alkyl group, and n represents an integer of 1-8.

8. A method according to claim 3, wherein a crude product of the fluoroalkanesulfinic acid ammonium salt obtained by claim 3 is extracted with an organic solvent, and a layer comprising the organic solvent is purified by washing with water.

9. A method according to claim 3, wherein a crude product of the fluoroalkanesulfinic acid ammonium salt obtained by claim 3 is extracted with an organic solvent, and a layer comprising the organic solvent is purified by washing with a thiosulfuric acid metal salt aqueous solution or sulfurous acid metal salt aqueous solution.

10. A method according to claim 4, wherein a crude product of the fluoroalkanesulfonic acid ammonium salt obtained by claim 4 is extracted with an organic solvent, and a layer comprising the organic solvent is purified by washing with water.

* * * * *